United States Patent [19]

Jendralla et al.

[11] Patent Number: 5,055,484
[45] Date of Patent: Oct. 8, 1991

[54] 7(1H-PYRROL-3-YL)-SUBSTITUTED 3,5-DIHYDROXYHEPT-6-ENOIC ACIDS, 7-(1H-PYRROL-3-YL)-SUBSTITUTED 3,5-DIHYROXYHEPT-ANOIC ACIDS, THEIR CORRESPONDING DELTA-LACTONES AND SALTS, THEIR USE AS MEDICAMENTS AND PHARMACEUTICAL PRODUCTS AND INTERMEDIATES

[75] Inventors: Heiner Jendralla; Gerhard Beck, both of Frankfurt am Main; Ekkehard Baader, Königstein; Bela Kerekjarto, Hofheim am Taunus, all of Fed. Rep. of Germany

[73] Assignee: Hoechst Aktiengesellschaft, Frankfurt am Main, Fed. Rep. of Germany

[21] Appl. No.: 216,423

[22] Filed: Jul. 8, 1988

[30] Foreign Application Priority Data

Jul. 10, 1987 [DE] Fed. Rep. of Germany ....... 3722806

[51] Int. Cl.$^5$ .................... A01N 43/36; A61K 31/40; C07D 405/06; C07D 207/30
[52] U.S. Cl. .................................. 514/422; 514/427; 548/517; 548/562
[58] Field of Search ................ 548/517, 562; 514/422, 514/427

[56] References Cited

U.S. PATENT DOCUMENTS

| 4,647,576 | 3/1987 | Hoefle | 548/517 |
| 4,681,893 | 7/1987 | Roth | 548/517 |
| 4,851,427 | 7/1989 | Wareing | 548/517 |

FOREIGN PATENT DOCUMENTS

| 0179559A2 | 4/1986 | European Pat. Off. . |
| 0221025 | 5/1987 | European Pat. Off. . |
| 0221025A1 | 5/1987 | European Pat. Off. . |
| 287890 | 10/1988 | European Pat. Off. . |

OTHER PUBLICATIONS

Phosphorus and the Related Group V Elements, E. Zbiral et al., vol. 2, No. 1, pp. 29-34, Jul. 1972.
Chemical Abstracts, vol. 93, 239089t, Dec. 22, 1980, European Search Report.
Stokker et al.; "3-Hydroxy-3-methylglutaryl-coenzyme A Reductase Inhibitors, 1. Structural Modification of 5-Substituted 3,5-Dihydroxypentanoic Acids and Their Lactone Derivatives", J. Med. Chem., vol. 28, (1985), pp. 347-358.
Hoffman et al., "3-Hydroxy-3-methylglutaryl-coenzyme A Reductanse Inhibitors, 2. Structural Modification of 7-(Substituted aryl)-3,5-dihydroxy-6-heptenoic Acids and Their Lactone Derivatives", J. Med. Chem., vol. 29, No. 2, (1986) pp. 159-169.
Stokker et al.; "3-Hydroxy-3-methylglutaryl-coenzyme A Reductase Inhibitors, 3. 7-(3,5-Disubstituted [1,1'-biphenyl]-2-yl)-3,5-dihydroxy-6-heptenoic Acids and Their Lactone Derivatives", J. Med. Chem., vol. 29, (1986), pp. 170-181.

Primary Examiner—Robert A. Wax
Assistant Examiner—Frederick F. Tsung
Attorney, Agent, or Firm—Finnegan, Henderson, Farabow, Garrett, and Dunner

[57] ABSTRACT

7-[1H-pyrrol-3-yl]-substituted 3,5-dihydroxyhept-6-enoic acids, 7-[1H-pyrrol-3-yl]-substituted 3,5-dihydroxyheptanoic acids of the formula I

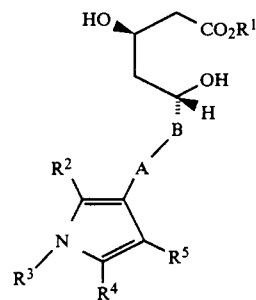

in which A, B, $R^1$, $R^2$, $R^3$, $R^4$ and $R^5$ have the indicated meanings, and the corresponding δ-lactones of the formula II

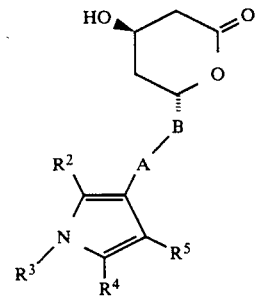

processes for the preparation of these compounds, their use as medicaments and pharmaceutical products are described. In addition, new intermediates for the preparation of the compounds of the formulae I and II are described.

4 Claims, No Drawings

7(1H-PYRROL-3-YL)-SUBSTITUTED 3,5-DIHYDROXYHEPT-6-ENOIC ACIDS, 7-(1H-PYRROL-3-YL)-SUBSTITUTED 3,5-DIHYROXYHEPT-ANOIC ACIDS, THEIR CORRESPONDING DELTA-LACTONES AND SALTS, THEIR USE AS MEDICAMENTS AND PHARMACEUTICAL PRODUCTS AND INTERMEDIATES

7-[1H-pyrrol-3-yl]-substituted 3,5-dihydroxyhept-6-enoic arids, 7-[1H-pyrrol-3-yl]-substituted 3,5-dihydroxyheptanoic acids, their corresponding 6-lactones and salts, processes for their preparation, their use as medicaments, pharmaceutical products and intermediates Hypercholesterolemia is one of the primary risk factors for cardiovascular disorders such as arteriosclerosis. It is known that the enzyme 3-hydroxy-3-methyl-glutaryl-coenzyme A reductase (HMG—CoA reductase) catalyzes the formation of mevalonic acid from 3-hydroxy-3-methylglutaryl-coenzyme A (HMG—CoA). This reaction plays a central part in the biosynthesis of cholesterol. Derivatives of 3-hydroxy-3-methylglutaric acid (HMG) and of mevalonic acid have been described as inhibitors of cholesterol biosynthesis. Such compounds take the form of, for example, the natural fermentation products compactin and mevinolin, a number of semisynthetic derivatives prepared therefrom, and various completely synthetic analogs.

Thus, for example, G.E. Stokker et al. (J. Med. Chem. 28, 347–358 (1985)) describe 3,5-dihydroxyhept-6(E)-enoic acids and 3,5-dihydroxyheptanoic acids which are substituted in the 7-position and in which the 7-substituent is phenyl, phenanthryl, decalinyl and adamantyl. W. F. Hoffmann et al. (J. Med. Chem. 29, 159–69 (1986)) describe 3,5-dihydroxyhept-6(E)-enoic acids substituted in the 7-position by substituted phenyl groups. In addition, G. E. Stokker et al. (J. Med. Chem. 29, 170–181 (1986)) report 3,5-dihydroxyhept-6(E)-enoic acids, and their δ-lactones, which are substituted in the 7-position by biphenyls. The compounds described by the said authors have only a weak inhibitory action on HMG—CoA reductase.

7-Substituted 3,5-dihydroxyheptanoic acids in which the 7-substituent is substituted 1H-pyrrolyl are described in European Patent Application with the publication no. 179,559; the pyrrole nitrogen is bonded to C-7 of the dihydroxyheptanoic acid (that is to say 1H-pyrrol-1-yl).

Finally, European Patent Application with the publication no. 221 025 claims, inter alia, 3,5-dihydroxyhept-6-enoic acids and 3,5-dihydroxyheptanoic acids which carry in the 7-position an optionally substituted 1H-pyrrol-2-yl or 1H-pyrrol-3-yl group. However, only compounds substituted with 1H-pyrrol-2-yl are described. Neither compounds substituted with 1H-pyrrol-3-yl nor processes for their preparation are disclosed.

Hence the invention relates to new 7-[1H-pyrrol-3-yl]-substituted 3,5-dihydroxyhept-6-enoic acids and 7-[1H-pyrrol-3-yl]-substituted 3,5-dihydroxyheptanoic acids, and their derivatives, of the general formula I

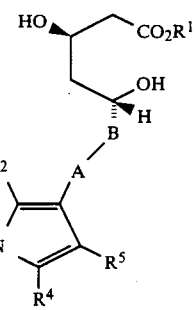

and to the corresponding δ-lactones of the formula II

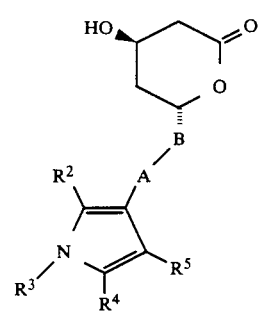

and to processes for their preparation. In the formulae,

A-B denotes an ethylenediyl group HC=CH or an ethanediyl group —$CH_2$—$CH_2$—, $R^1$ denotes H, alkyl having 1 to 4 carbon atoms, phenyl, benzyl or 2,3-dihydroxypropyl, or a pharmacologically tolerated alkali or alkaline earth metal cation, $NH_4^+$ or an ammonium ion substituted with 1 to 4 alkyl groups each having 1–4 carbon atoms, $R^2$, $R^3$, $R^4$ and $R^5$ denote, independently of one another, 1) hydrogen
2) straight-chain or branched alkyl having 1–12 carbon atoms, or cycloalkyl which has 5–7 carbon atoms and is optionally bonded via a straight-chain or branched alkyl chain of 1–5 carbon atoms to the aromatic heterocycle,
3) phenyl or benzyl, unsubstituted or substituted 1–3 times with
   a) fluorine, chlorine, bromine or trifluoromethyl,
   b) alkyl or alkenyl having up to 5 carbon atoms, it being possible for ortho alkyl or alkenyl substituents to be connected with the formation of a fused-on carbocyclic ring,
   c) alkoxy having 1–5 carbon atoms or
   d) alkoxycarbonyl having 2–6 carbon atoms.

Examples of groups $R^2$ and $R^5$ defined as under 3)b) have the following formulae:

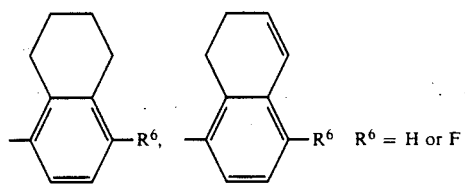

The radicals preferably have the following meanings:
A-B —HC=CH— or —$CH_2$—$CH_2$—

$R^1$ methyl, ethyl or Na $R^2$, $R^3$, $R^4$ and $R^5$, independently of one another,
1) hydrogen
2) methyl, ethyl, isopropyl, tert.-butyl or cyclohexyl, or
3) phenyl which can be substituted once or twice by
   a) fluorine or chlorine, or
   b) methyl.

Among the radicals mentioned for the general formulae I and II, the following are particularly preferred:

A-B trans —CH=CH—

$R^1$ methyl, ethyl or Na $R^2$ and $R^5$, independently of one another, isopropyl, p-fluorophenyl, p-fluoro-m-methylphenyl, and $R^3$ and $R^4$, independently of one another, hydrogen, iso propyl, cyclohexyl and phenyl.

The invention relates to the pure enantiomers as well as the racemates of the formula I, and mixtures thereof, that is to say the racemates with the absolute configuration 3R/5S and 3S/5R for A-B equal to —CH=CH—and
3R/5R and 3S/5S for A-B equal to —CH$_2$—CH$_2$—
and the pure enantiomers
3R/5S for A-B equal to —CH=CH—and
3R/5R for A-B equal to —CH$_2$—CH$_2$—.

The invention further relates to the pure enantiomers and to the racemates of the general formula II derived from the abovementioned stereoisomeric open-chain dihydroxy carboxylic acids of the general formula I. These are, specifically, the racemates with the absolute configurations 3R/5S and 3S/5R for A-B equal to —CH=CH— and
3R/5R and 3S/5S for A-B equal to —CH$_2$—CH$_2$— and the pure enantiomers 3R/5S for A-B equal to —CH=CH— and
3R/5S for A-B equal to —CH=CH— and When A-B in the formulae I or II denotes —HC=CH—, this group can have a trans configuration

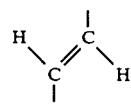

or a cis configuration

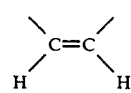

The invention relates to both diastereomers. However, the diastereomer having the trans configuration of the double bond is preferred.

The compounds of the formulae I and II are strong inhibitors of HMG—CoA reductase.

Hence the invention further relates to the use of these compounds, in particular for the treatment of hypercholesterolemia, and to pharmaceutical products.

The processes for the preparation of the compounds of the formulae I and II comprise A) 1. reduction of a carbaldehyde of the formula III

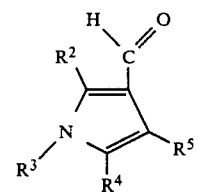

to an alcohol of the formula IV

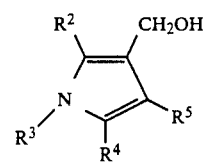

2. conversion of the alcohol IV into the halogen derivative of the formula V

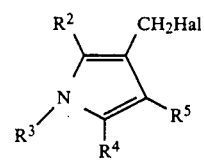

in which Hal denotes chlorine, bromine or iodine, 3. conversion of the halogen compounds of the formula V into the phosphonium salt of the formula VI

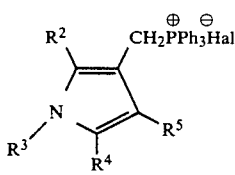

in which Hal denotes chlorine, bromine or iodine, 4. reaction of the phosphonium salt of the formula VI with the compactin aldehyde of the formula VII

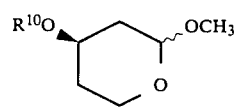

in which $R^{10}$ denotes a protective group which is stable to bases and weak acids, for example t-butyldiphenylsilyl, to give the lactol ether of the formula VIII

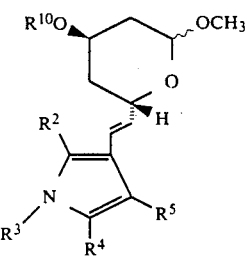

5. acid hydrolysis of the methyl acetal group in the lactol ether of the formula VIII to give a lactol of the formula IX

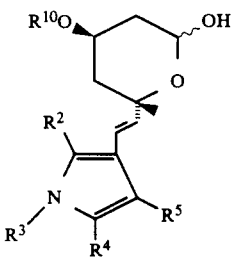

IX 6. oxidation of the lactol of the formula IX to a lactone of the formula X

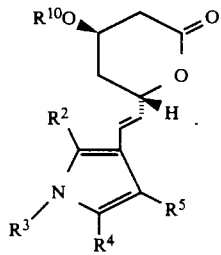

X 7. elimination of the protective group $R^{10}$, for example

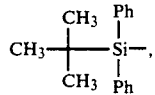

in the lactone of the formula X to give a compound of the formula II

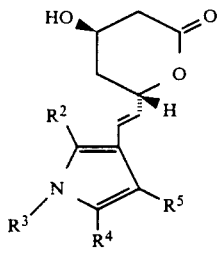

II in which $R^2$ to $R^5$ have the indicated meanings, and A-B denotes the —CH=CH— group, and 8. where appropriate conversion of a resulting compound of the formula II in which $R^2$ to $R^5$ have the indicated meanings (and A-B represents the —CH=CH group into the corresponding dihydroxyhept-6-enoic acid of the formula I

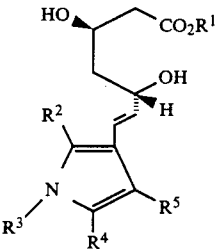

I in which $R^1$ to $R^5$ have the indicated meanings (and A-B represents the —CH=CH— group), and 9. where appropriate hydrogenation of the double bond in a resulting compound of the formula I or II with A-B equal to —CH=CH— to give a compound of the formula I or II with A-B equal to —$CH_2$—$CH_2$—, it being possible for the hydrogenation also to be carried out on the intermediates VIII, IX or X, as well as before the conversion of compounds II into I, or B) 1. subjecting the α,β-unsaturated aldehyde of the formula XI

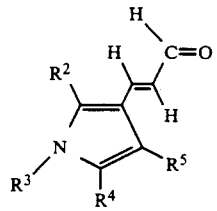

XI to an aldol reaction with the dianion of methyl acetoacetate, resulting in a compound of the formula XII

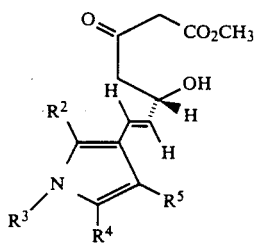

XII 2. stereoselective reduction of the keto group in a compound of the formula XII to give a compound of the formula I

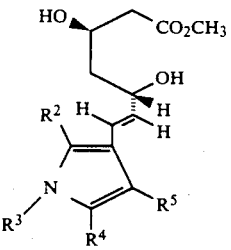

I in which $R^2$ to $R^5$ have the indicated meanings, $R^1$ is the methyl group and A-B is the —C=CH— group, 3. where appropriate conversion of a resulting compound of the formula I in which $R^1$ denotes the $CH_3$ group, and A-B denotes the —CH=CH— group, into a compound I in which $R^1$ to $R^5$ have the meanings indicated for formula I, and A-B represents the —CH=CH— group, and 4. where appropriate hydrogenation of the double bond in a resulting compound of the formula I with A-B equal to —CH=CH— to give a compound of the formula I with A-B equal to —CH$_2$—CH$_2$—, and 5. where appropriate conversion of a resulting compound of the formula I with $R^1$=H, with elimination of water, into a lactone of the formula II, or C) 1. reaction of the enolate of an acetic ester of the formula XIII

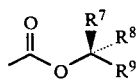

XIII in which $R^7$ denotes a phenyl ring which is unsubstituted or substituted by fluorine, chlorine, bromine or branched or unbranched alkyl having 1–4 carbon atoms, $R^8$ denotes an H atom or methyl, and $R^9$ denotes diphenylhydroxymethyl Ph$_2$COH, the phenyl rings being unsubstituted or substituted by fluorine, chlorine, bromine or branched or unbranched alkyl having 1–4 carbon atoms, in an aldol reaction with the α,β-unsaturated aldehyde of the formula XI

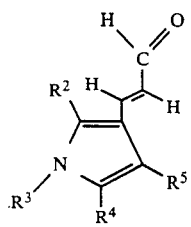

XI to give the adduct of the formula XIV

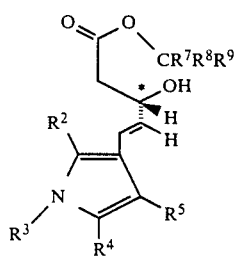

XIV in which $R^2$ to $R^5$ have the meanings indicated &or formula I, and $R^7$, $R^8$ and $R^9$ have the meanings indicated for formula XIII, 2. conversion of the adduct of the formdula XIV, by transesterification, into the 8-hydroxy methyl ester of the formula XV

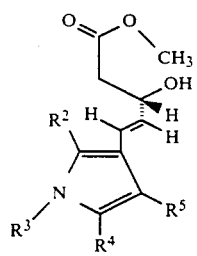

XV 3. conversion of the resulting methyl ester of the formula XV, using the enolate of an alkyl acetate, into the 8-keto-β-(S)-hydroxy ester of the formula XVI

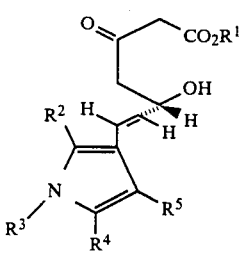

XVI in which $R^2$ to $R^5$ have the meanings indicated for formula I, and $R^1$ is an alkyl group having 1-4 carbon atoms, and 4. stereoselective reduction of the keto group in a resulting compound of the formula XVI to give a compound of the formula I

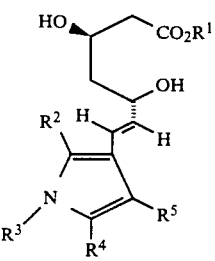

I in which $R^2$ to $R^5$ have the meanings indicated for formula I, $R^1$ is an alkyl group having 1–4 carbon atoms (and A-B is the —CH=CH— group), 5. where appropriate conversion of a resulting compound of the formula I in which $R^1$ is an alkyl group having 1–4 carbon atoms, and A-B denotes the —CH=CH— group, into a compound of the formula I in which $R^1$ to $R^5$ have the meanings indicated for formula I, and A-B represents the —CH=CH—group, and 6. where appropriate hydrogenation of the double bond in a resulting compound of the formula I with A-B equal to —CH=CH— to give a compound of the formula I with A-B equal to —CH$_2$—CH$_2$—, and 7. where appropriate conversion of a resulting compound of the formula I with $R^1$=hydrogen, with eliminination of water, into a lactone of the formula II.

Process A, depicted in scheme 1, in which some compounds are defined more strictly, is based on Wittig coupling of the ylid generated from the phosphonium salt VI with the protected, optically pure "compactin aldehyde" VII. See J. R. Falck, Tetrahedron Lett. 23, 4305 (1982) and European Patent Application with the publication no. 217 092 for the synthesis of VII from tri-O-acetyl-D-glucal. The advantage of this process is that optically active final products of the general formula I are obtained directly in the desired absolute configuration. As a rule, mixtures of the cis and trans isomer are obtained when VI is coupled with VII. In addition, hydrolysis of the lactol ether VIII to the lactol IX requires a moderately to strongly acidic medium. Under these conditions, 1H-pyrroles undergo substantial hydrolysis. Using this process, the compounds of the formula I and II are obtained.

Scheme 1:
Process A for the synthesis of compounds of the general formulae I and II from heterocyclic aldehydes III
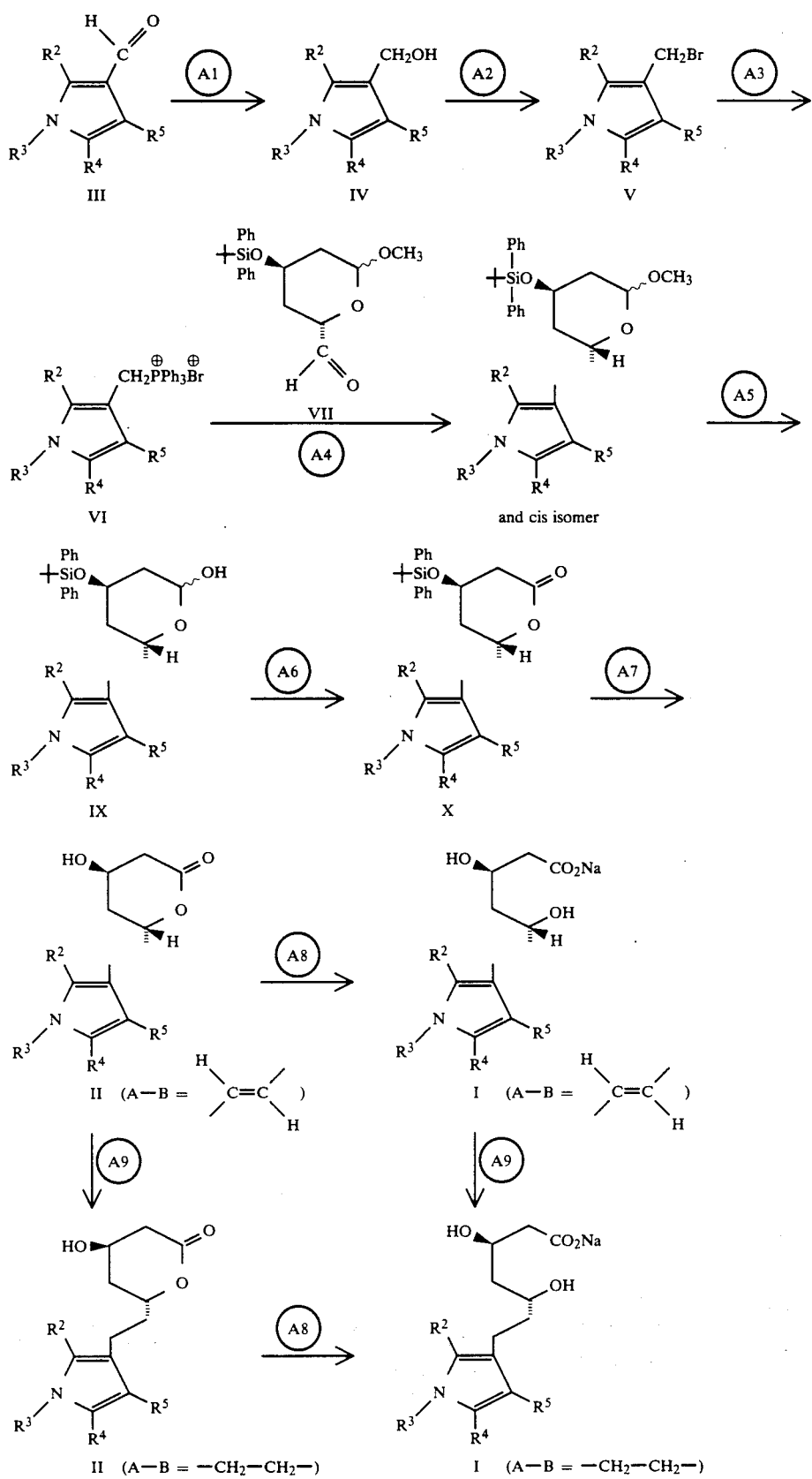

Compounds of the formula I are advantageously prepared by processes B and C. Processes B and C start from the α,β-unsaturated aldehyde of the formula XI. The latter is obtained, for example, by using the "Wollenberg reagent" (R.H. Wollenberg et al., J. Am. Chem. Soc. 99, 7365 (1977)) to extend the carbaldehyde III. The reaction follows the equation:

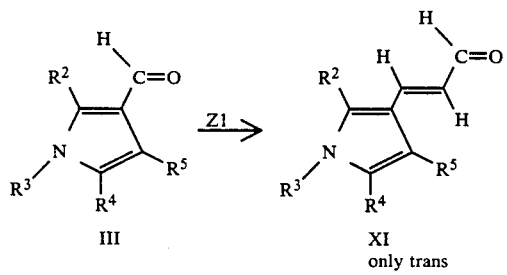

Another process for the preparation of the compound XI is based on the base-catalyzed Emmons-Horner coupling of the carbaldehyde III with a cyanomethylphosphonate, preferably diisopropyl cyanomethylphosphonate (commercially available). The resulting 3-heteroaryl-substituted acrylonitriles XVII can then be reduced with various reducing agents, preferably diisobutylaluminum hydride, to the aldehydes XI. The following equation applies to the reaction:

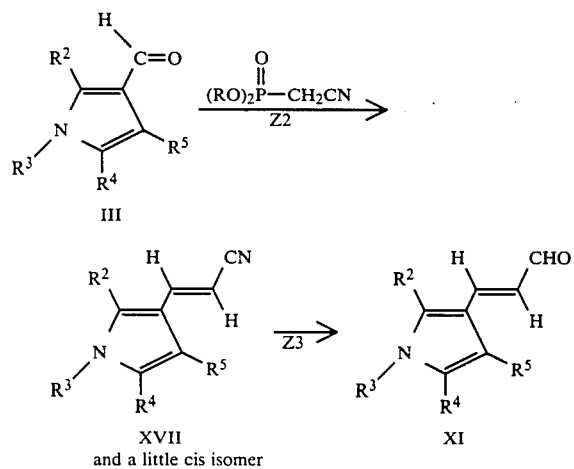

The yields in the preparation of XI are lower in the latter process. The trans/cis selectivity is high.

In process B, the aldehyde XI undergoes an aldol reaction with the dianion of methyl acetoacetate. The subsequent stereoselective reduction of the keto group results in compounds of the formula I. The advantages of this process are that the introduction of the double bond (AB=—HC=CH—) takes place with a yield exceeding 95%, and that the double bond has, within the range of analytical accuracy, only the desired trans configuration. Another advantaee of the process is that all the process steps can be carried out under basic to neutral conditions, at or below room temperature.

The final products of the general formula I can be obtained optically pure in the desired absolute configuration by subjecting the racemic products I to racemate resolution, for example using d(+)-α-methylbenzylamine as proposed in U.S. Pat. No. 4,567,289.

Process C, depicted in Scheme 2 (B2 and A9 relate to steps mentioned in processes B and A, respectively), comprises reaction of the enolate of an acetic ester, preferably the magnesium enolate of an acetic ester having an optically active alcohol component, particularly preferably the magnesium enolate of S(+)-2-acetoxy-1,1,2-triphenylethanol (Thesis, R. M. Devant, Univ. Karlsruhe (1985), pages 96–98), by the procedure of Braun and Devant (Tetrahedron Lett. 25, 5031 (1984)) or of Lynch et al. (Tetrahedron Lett. 28, 1385 (1987)) in an aldol reaction with the α,β-unsaturated aldehyde XI to give the adduct XIV. When the magnesium enolate of S(+)-2-acetoxy-1,1,2-triphenylethanol is used, this addition is highly diastereoselective, and the result is that 90–97% of the chirality center in XIV is in the desired S configuration. Transesterification to the methyl ester XV, followed by Claisen condensation with the enolate of an alkyl acetate, preferably the lithium enolate of tert.butyl acetate, provides the β-keto-δ-(S)-hydroxy ester XVI which can (in analogy to process B) be reduced stereo-selectively to the 3(R),5(S)-dihydroxyhept-6(E)-enoic ester I. Basic hydrolysis or hydrogenation of the resulting compounds provides the products of the general formula I with a high excess of the desired enantiomer (>80% ee). The optically pure compounds can be obtained therefrom by recrystallization.

Scheme 2: Process C for the synthesis of compounds of the general formula I from 3-heteroaryl-substituted E-propenals XI

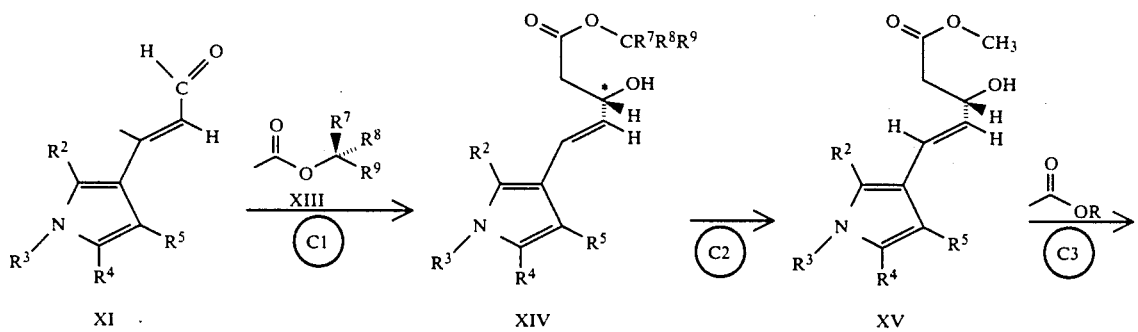

Scheme 2: Process C for the synthesis of compounds of the general formula I from 3-heteroaryl-substituted E-propenals XI

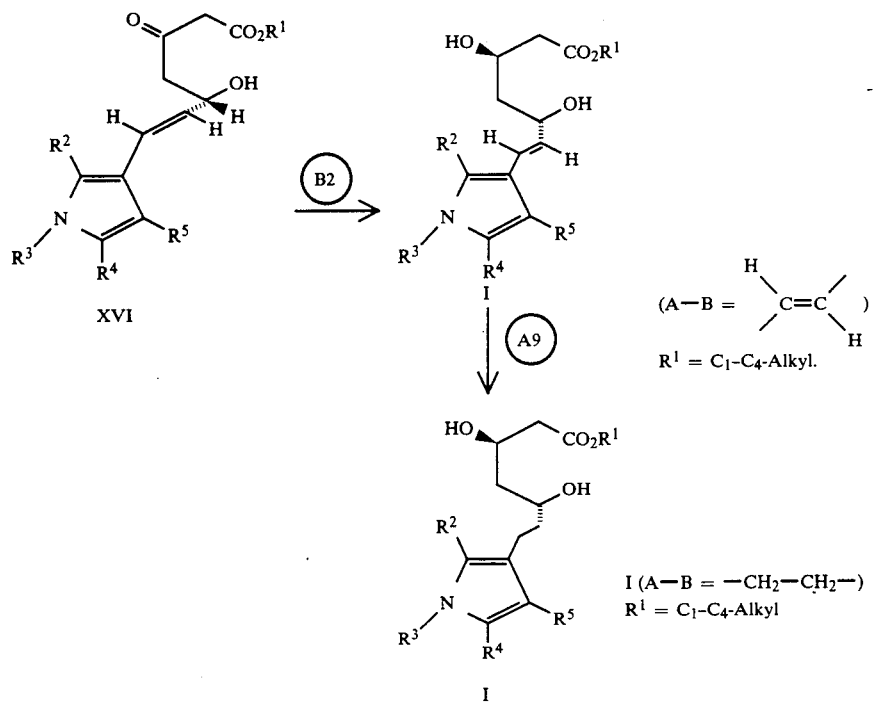

R², R³, R⁴ and R⁵ in formulae III–XVII have the same meanings as indicated for formulae I and II (see above). $R^7$ denotes a phenyl ring which is unsubstituted or can be substituted by fluorine, chlorine, bromine or branched or unbranched alkyl having 1–4 carbon atoms. $R^7$ preferably denotes unsubstituted phenyl. $R^8$ denotes an H atom or methyl, preferably an H atom. $R^9$ denotes diphenylhydroxymethyl $PH_2COH$, the phenyl rings preferably being unsubstituted, or possibly being substituted by fluorine, chlorine, bromine, or branched or unbranched alkyl having 1–4 carbon atoms.

The compounds of the formulae VI, VII–XI and XIV, XVI and XVII are new and are, for example, valuable intermediates for the preparation of compounds of the formula I and II. Hence the invention also relates to the compounds of the formulae VI, VIII–XI and XIV, XVI and XVII, and to processes for their preparation (compounds of the formula XII (XV) are a special case of compounds of the formula XVI).

Heterocyclic aldehydes of the general formula III are required as starting materials for process A for the synthesis of products of the general formulae I and II and for the preparation of α,β-unsaturated aldehydes of the formula XI.

Heterocyclic aldehyes of the general formula III in which the substituents $R^2$–$R^5$ have the same meaning as indicated for the general formulae I and II can be obtained in various ways, which are compiled in Scheme 3.

Scheme 3: Processes for the synthesis of the aldehydes of general formula III

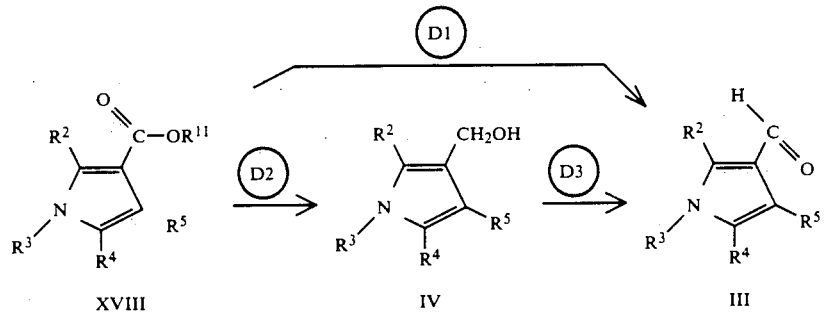

-continued
Scheme 3: Processes for the synthesis of the aldehydes of general formula III

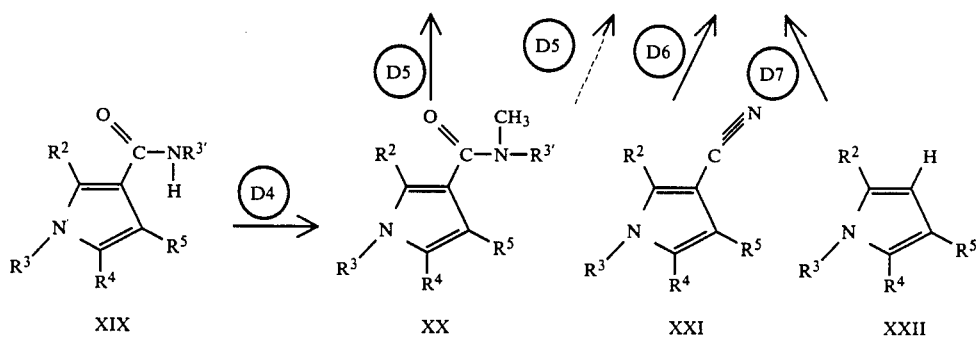

$R^{3'}$ in the formulae XIX and XX denotes phenyl or phenyl which is substituted by the groups mentioned for formula I under a) to d).

Heterocyclic alkyl carboxylates of the general formula XVIII ($R^{11}=C_1-C_4$-alkyl), preferably the methyl esters ($R^{11}=CH_3$), can, under certain conditions, be reduced directly to the aldehyde of the general formula III (D1). (See, for example, G. Benz in Houben-Weyl Volume E3, Thieme Verlag (1983), pages 437–450). However, it is preferable first to reduce the ester XVIII to the alcohol IV, and then oxidize to the aldehyde III. A large number of methods exist both for the reduction step D2 and for the oxidation step D3 (see, for example, A. Hajós in Houben-Weyl Vol. IV/1d Part II, Thieme Verlag (1981), pages 195–199; H. Bornowski in Houben-Weyl Vol. E3, Thieme Verlag (1983), pages 265 et seq., and E. Campaigne, G. M. Shutske, J. Heterocyclic Chem. 12, 317 (1975)).

The reduction D2 is preferably carried out with lithium aluminum hydride or with diisobutylaluminum hydride, and the oxidation D3 is preferably carried out with manganese dioxide or with chromium trioxide in pyridine. Alternatively. the oxidation D3 can be carried out with the Fetizon reagent ($Ag_2CO_3$ on Celite, see M. Fetizon et al., Compt. Rend. Acad. Sc. Paris, Ser. C, 267, 900 (1968) and J. Heterocyclic Chem. 13, 525 (1976)) or with pyridinium chlorochromate (G. Piancatelli et al. Synthesis, 245 (1982)) or with pyridinium dichromate (E. J. Corey et al., Tetrahedron Lett. 20, 399 (1979)), by Swern oxidation (D. Swern et al., Synthesis, 165 (1981)) or with N-methylmorpholine N-oxide with ruthenium catalysis (K. B. Sharless et al., Tetrahedron Lett. 17, 2503 (1976); H. Tomioka et al., Tetrahedron Lett. 22, 1605 (1981)).

It is particularly preferred to carry out the reduction step D2 with lithium aluminum hydride, and the oxidation step D3 with manganese dioxide or with N-methylmorpholine N-oxzide/tris(triphenylphosphine)ruthenium(II) chloride.

Aldehydes of the general formula III can also be obtained from alides of the general formula XIX by converting the latter into the N-methylanilides XX and reducing the latter with lithium aluminium hydride to alcohols of the general formula IV (D4, D5). Depending on the nature of the substituents $R^2-R^5$, this reduction may also, in some systems, result directly in the aldehyde III (F. Weygand, Angew, Chem. 65, 525 (1953)). Heterocyclic nitriles of the general formula XXI can be reduced with complex metal hydrides, preferably with diisobutylaluminum hydride, to aldehydes of the formula III.

Electron-rich heterocycles of the general formula XXII can, in some cases, be converted by a Vilsmeier formylation into aldehydes of the formula II (D7) (see, for example, G. Simchen in Houben-Weyl, Vol. E3, Thieme Verlag (1983), pages 57 et seq.).

The reaction conditions for carrying out the process steps indicated in process A (Scheme 1), process B (including preparation of the starting compound in steps Z1, Z2 and Z3), process C (Scheme 2) and Scheme 3 can be found in Table 1 and the examples (see thereafter).

TABLE 1

| Process steps | Reagent (equiv.) | Temperature | Solvent | Inert atmosphere |
|---|---|---|---|---|
| A1 | complex metal hydride (excess), preferably LiAlH$_4$ | −20° C. to reflux, preferably 25° C. | ether, THF, benzene or toluene, preferably ether | yes |
| A2 | PBr$_3$ (0.5) | 0–25° C. | benzene or toluene | — |
| A3 | PPh$_3$ (excess) | 60–120° C., preferably 80° C. | benzene or toluene | — |
| A4 | a) n-BuLi (1.0)<br>b) VII (0.9) | a) heat VI to ~120° C./2 h, n-BuLi at 5–10° C., then 25° C./30 min<br>b) VII at 25° C. | ether, THF, benzene, toluene, preferably THF | yes |
| A5 | H$_2$O/AcOH (excess) or CF$_3$CO$_2$H (excess) | 25° C.-reflux, preferably about 60° C.<br>0–50° C., preferably 0–20° C. | H$_2$O/THF, preferably about 1:1 | yes |
| A6 | (n-Bu)$_4$NI (1.0) N-iodosuccinimide | 0–50° C., preferably 25° C. | inert solvent, preferably CH$_2$Cl$_2$ | yes<br>yes |

TABLE 1-continued

Process steps for the synthesis of compounds of the general formula I

| Process steps | Reagent (equiv.) | Temperature | Solvent | Inert atmosphere |
|---|---|---|---|---|
| | (~5.0) or CrO$_3$ (10.0), pyridine (20.0) | 0–30° C., preferably 25° C. | CH$_2$Cl$_2$ | — |
| A7 | (n-Bu)$_4$NF.3H$_2$O (~3.0)AcOH (~4.0) or | −30° C.−+50° C. preferably 0–25° C. | ether, THF, benzene or toluene, preferably THF | yes |
| | 48% HF/H$_2$O (excess) | 0–80° C. preferably 25° C. | CH$_3$CN | — |
| A8 | NaOH (1.0) | 0–50° C., preferably 25° C. | H$_2$O, CH$_3$OH or EtOH | — |
| A9 | Pd/C, H$_2$, 1 atm | 0–50° C. preferably 25° C. | inert solvent, preferably CH$_3$OH, trace of NEt$_3$ | — |
| Z1 | 1-tri-n-butylstannyl-2-ethoxyethylene (1.2) n-BuLi (1.25) | −78° C.−−40° C. preferably −70° C. | ether or THF, preferably THF | yes |
| B1 | CH$_3$—C(=O)—CH$_2$—CO$_2$CH$_3$ (1.75) NaH (1.80) n-BuLi (1.70) | a) NaH at −15° C./ 50 min<br>b) n-BuLi at −15° C./ 20 min<br>c) aldehyde at −15° C. ⟶ 0° C./ 45 min<br>d) NaH$_2$PO$_4$/H$_2$O (excess) −10° C. ⟶ 25° C. | ether or THF, preferably THF | yes |
| B2 | Et$_3$B (1.2) NaBH$_4$ (1.3) | a) Et$_3$B at 25° C./ 20 min<br>b) NaBH$_4$ at ~70° C./ 12 h<br>c) NaH$_2$PO$_4$/H$_2$O (excess) at −10° C. | ether or THF, preferably THF | yes |
| Z2 | NaH (1.8) ((CH$_3$)$_2$CHO)$_2$POCH$_2$CN (1.5) | a) phosphonate at 0° C. to NaH; 40 min 0° C.<br>b) aldehyde at 0° C.; 1–3 h 25° C. | ether or THF, preferably THF | yes |
| Z3 | ((CH$_3$)$_2$—CH—CH$_2$)$_2$AlH (3.0) | −20−+50° C., preferably 0° C. | inert solvent, preferably THF | — |
| C1 | S(+)CH$_3$CO$_2$CH(Ph)C(OH)Ph$_2$ (1.1)<br><br>LDA (2.5)<br>MgI$_2$ + Et$_2$O (1.1) | −135° C. to −60° C., preferably −78° C. see thesis R. M. Devant, Univ. Karlsruhe (1985), pages 99–101 | ether or THF, preferably THF | yes |
| C2 | CH$_3$ONa (1.05) | 0–65° C., preferably 25° C. | CH$_3$OH | — |
| C3 | CH$_3$—C(=O)—O-tert.butyl (3.0) n-BuLi (2.9) | −10−−50° C., preferably −30° C./1 h | ether or THF, preferably THF | yes |
| D1 | ((CH$_3$)$_2$CHCH$_2$)$_2$AlH (1.0) | −40−−78° C., preferably −78° C. | inert solvent, preferably THF | yes |
| D2 | complex metal hydride, preferably LiAlH$_4$ (excess) or | −20° C. to reflux, preferably 25° C. | ether, THF, benzene or toluene, preferably ether | yes |
| | ((CH$_3$)$_2$CHCH$_2$)$_2$AlH (4.0) | −40° C. | inert solvent, preferably toluene | yes |
| D3 | MnO$_2$(excess) or | 0–35° C., preferably 25° C. | ether | — |
| | CrO$_3$(10.0), pyridine (20.0) | 0–25° C., preferably 25° C. | CH$_2$Cl$_2$ | — |
| D4 | NaH (excess) CH$_3$I (excess) | a) NaH 25° C. ⟶ 110° C.<br>b) CH$_3$I 25° C. ⟶ reflux | toluene | — |
| D5 | LiAlH$_4$ (3.0) | reflux | THF | yes |
| D6 | ((CH$_3$)$_2$CHCH$_2$)$_2$AlH (1.3) | −50° C.-0° C. preferably −30° C. | THF or toluene | yes |
| D7 | HCON(CH$_3$)$_2$ (3.0) | −40° C.−+50° C. | inert solvent, | yes |

TABLE 1-continued

Process steps for the synthesis of compounds of the general formula I

| Process steps | Reagent (equiv.) | Temperature | Solvent | Inert atmosphere |
|---|---|---|---|---|
| | POCl$_3$ (3.2) | preferably 0° C. | e.g. CH$_3$CN | |

Heterocyclic alkyl esters of the general formula XVIII, antilides of the general formula XIX, nitriles of the general formula XXI and heterocycles of the general formula XXII can be obtained by a number of general heterocyclic syntheses. These are state of the art and can be found in monographs on the relevant heterocycles.

A selection of synthetic methods is indicated hereinafter, these being particular suitable for the preparation of those compounds of the egneral formulae XVIII, XIX, XXI or XXII which are, in terms of their substituents R$^2$, R$^3$, R$^4$ and R$^5$, preferred or particularly preferred.

Scheme 4: Synthesis of intermediates of the 1H-pyrrol-3-yl type

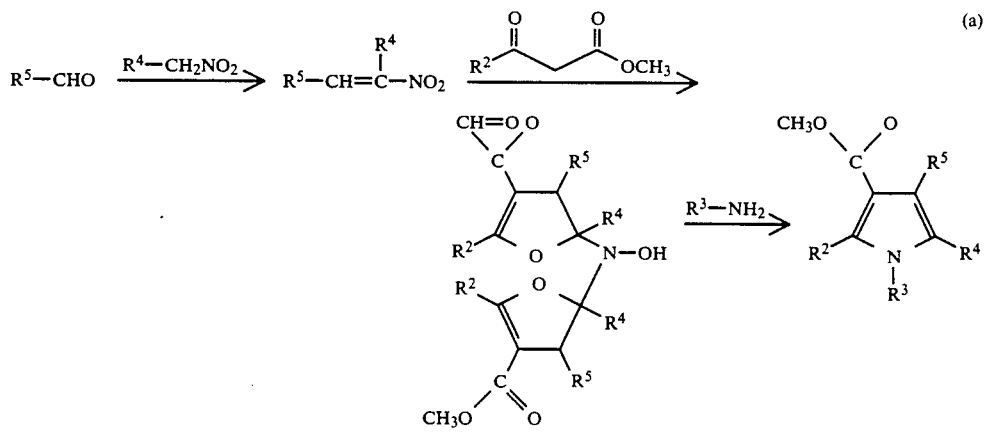

(a)

see A. Gomez-Sanchez et. al., J. Chem. Soc Perkins Trans. I. 441 (1982)

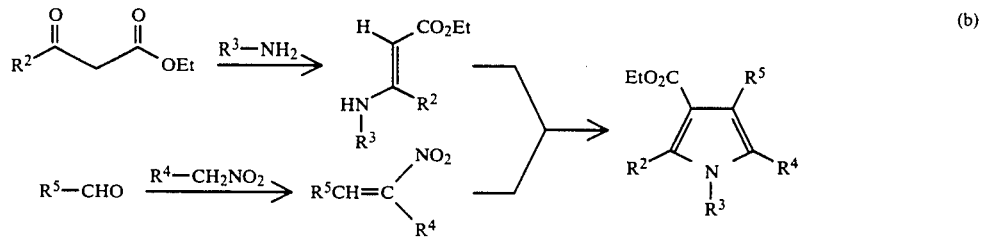

(b)

See H. Meyer, Liebigs Ann. Chem. 1981, 1534

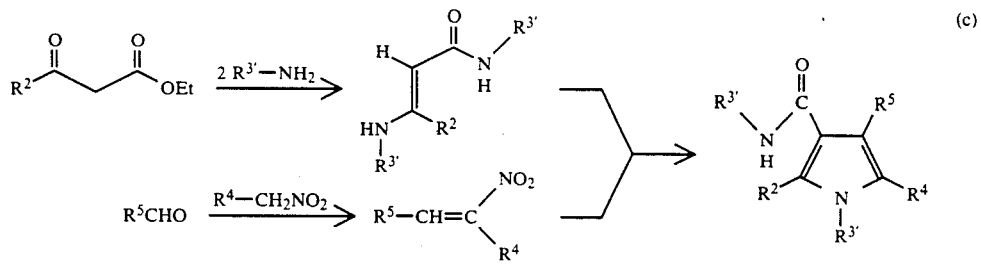

(c)

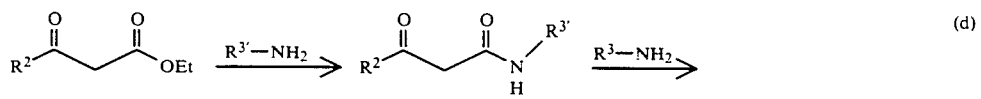

(d)

-continued
Scheme 4: Synthesis of intermediates of the 1H-pyrrol-3-yl type

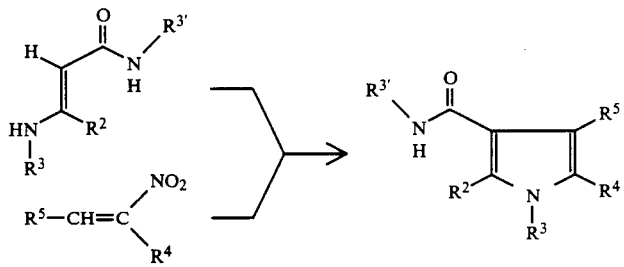

R3' denoting phenyl or phenyl which is substituted by the groups mentioned for formula I under a)–d), Preparation of

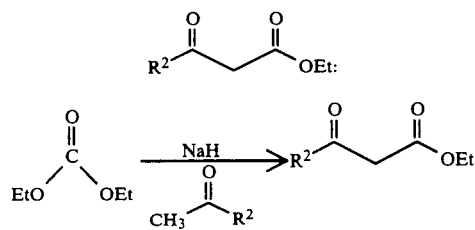

see N, Jackman et al., J. Am. Chem. Soc. 70, 2885 (1948)

In method b), the β-keto ester is reated with 1 equivalent of the amine to give the enamino ester when $R^2$ is not sterically demanding (for example $R^2=CH_3$). On the other hand, if $R^2$ is a bulky substituent (for example $R^2=$isopropyl, method c), then, in the case of aniline, the attack on the ester group takes place more quickly than that on the keto group. If $R^3$ is a substituted or unsubstituted phenyl ring, then, by use of two equivalents of the aniline $R^{3'}$—$NH_2$, the enamino acid anilide ($R^3=R^{3'}$) (method c) is obtained directly, and is condensed with the nitro compound to give the 3-pyrrolecarboxanilide. On the other hand, if $R^3$ is an alkyl radical, and thus necessarily different from $R^{3'}$ (method d), it is necessary first to react the β-keto ester with one equivatent of the aniline $R^{3'}$—$NH_2$ to give the β-keto anilide, which then condenses with one equivalent of the alkylamine $R^3$—$NH_2$ to give the enamino acid anilide ($R^3 \neq R^{3'}$)

The inhibition of HMG—CoA reductase activity by the compounds of the general formulae I and II was determined on solubilized enzyme preparations from rat liver microsomes.

After a changeover in the day/night rhythm of the rats, enzyme production was induced with cholestyramine (®Cuemid) The substrate used was (S,R) $^{14}C$—HMG—CoA, and the concentration of NADPH was maintained by a regenerating system during the incubation. $^{14}C$-mevalonate was removed from substrate and other products (for example $^{14}C$—HMG) by column elution, with the elution profile of each individual sample being determined. Inclusion of $^3H$-mevalonate throughout was dispensed with because the data to be determined were of the relative inhibitory effect. In each test series the enzyme-free control, the enzyme-containing normal mixture ($=100\%$) and those with added products were treated together. Each individual value was formed as the mean of 3 parallel samples. The t test was used to assess the significance of the differences between the means for product-free and product-containing samples.

The method described above was used to determine, for example, the following figures for the inhibiticn of HMG—CoA reductase by the compounds according to the invention ($IC_{50}$ value M=molar concentration of the compound necessary for 50% inhibition. In each case, the $IC_{50}$ values for the optically pure compounds I in the preferred absolute configuration are indicated).

TABLE 2

| Example | $IC_{50}$ (M) |
|---|---|
| 1 | $3.2 \times 10^{-7}$ |
| 2 | $1.2 \times 10^{-7}$ |
| 3 | $8.0 \times 10^{-8}$ |
| 4 | $8.7 \times 10^{-9}$ |
| 5 | $7.0 \times 10^{-9}$ |
| 6 | $3.0 \times 10^{-9}$ |
| 7 | $8.0 \times 10^{-9}$ |
| 8 | $2.5 \times 10^{-9}$ |
| 9 | $1.2 \times 10^{-7}$ |
| 10 | $9.5 \times 10^{-9}$ |
| 11 | $8.0 \times 10^{-9}$ |
| 12 | $3.5 \times 10^{-9}$ |
| 13 | $1.5 \times 10^{-8}$ |
| 14 | $3.0 \times 10^{-9}$ |
| 15 | $7.0 \times 10^{-8}$ |
| 16 | $1.6 \times 10^{-7}$ |
| 17 | $1.0 \times 10^{-7}$ |
| 18 | $5.0 \times 10^{-8}$ |
| 20 | $1.2 \times 10^{-8}$ |
| 22 | $1.5 \times 10^{-9}$ |
| 24 | $1.9 \times 10^{-8}$ |
| 26 | $3.0 \times 10^{-9}$ |

In addition, the inhibition of cholesterol biosynthesis by selected compounds was tested by the incorporation of $^{14}C$-precursor in cholesterol in cell cultures.

Monolayers of HEP G2 cells in lipoprotein-free nutrient medium were preincubated with various concentrations of the test substances for 1 hour. The $^{14}C$-labeled precursor sodium $^{14}C$-acetate was added, and the incubation was then continued for 3 hours. Subsequently 3H-cholesterol was added as internal standard, and a portion of these cells underwent alkaline hydrolysis. The lipids from the hydrolyzed cells were extracted with chloroform/methanol. Carrier cholesterol was added to this lipid mixture which was then subjected to preparative thin-layer chromatography, the cholesterol band was visualized with iodine vapor and then isolated, and the amount of $^{14}C$-cholesterol formed from the $^{14}C$-precursor was determined by scintigraphy. Cellular protein was determined in an aliquot of the cells, so that the amount of $^{14}C$-cholesterol formed from $^{14}C$-precursor in unit time per mg of cellular protein can be calculated. The solvent control is used for comparison of the inhibitory effect of an added test product, so that it is possible to state directly the inhibition of cholesterol biosynthesis at a particular molar concentration of the test product in the medium. The integrity of the cell culture and the absence of cell damage due to exposure to the products was checked morphologically (light microscope) in an aliquot of the cell cultures. Table 3 shows the potency of the test compounds relative to that of mevinolin sodium salt. The relative potency was determined by comparing the $IC_{70}$ values and $IC_{50}$ values for the test compound and for mevinolin sodium salt (internal standard). The absolute values for $IC_{70}$ and $IC_{50}$ (mevinolin sodium) vary somewhat from cell culture to cell culture. The mean figures are $IC_{70}=1.5\times 10^{-7}M$, $IC_{50}=5\times 10^{-8}M$.

TABLE 3

| Example | % potency relative to mevinolin sodium | |
|---|---|---|
|  | at $IC_{70}$ | at $IC_{50}$ |
| 1 | 180 |  |
| 4 | 51 | 450 |
| 12 | 350 |  |
| 14 | 150 |  |

The compounds of the general formula I or II are distinguished by strong inhibition of HMG—CoA reductase, the rate-determining enzyme of cholesterol biosynthesis. The enzyme HMG—CoA reductase is widespread in nature. It catalyses the formation of mevalonic acid from HMG—CoA. This reaction is a central step in cholesterol biosynthesis (cf. J. R. Sabine in CRC Series in Enzyme Biology: 3-Hydroxy-3-methylgluraryl coenzyme A reductase, CRC Press Inc. Boca Raten, Fla. 1983 (ISBN 0-8493-6551-1)).

High cholesterol levels are thought to be associated with a number of diseases such as, for example, coronary heart disease or arteriosclerosis. This is why the lowering of elevated cholesterol levels is a therapeutic aim for the prevention and treatment of such diseases.

One starting point for this comprises inhibition or reduction of endogenous cholesterol biosynthesis. Inhibitors of HMG—CoA reductase block cholesterol biosynthesis at an early stage.

Hence the compounds of the general formula I or II are suitable as hypolipidemics and for the treatment or prophylaxis of arteriosclerotic changes.

Hence the invention also relates to pharmaceutical products based on these compounds, and to their use as medicaments, in particular as hypolipidemics and for the prophylaxis of arteriosclerotic changes.

Compounds of the formula I or II are used as hypolipidemics or antiarteriosclerotics in oral doses of 3 to 2,500 mg, but preferably in the dose range 10-500 mg. These daily doses can, if required, also be divided into two to four single doses or incorporated in a sustained release form. The dosage regimen may depend on the type, age, weight, sex and medical condition of the patient.

An additional cholesterol-lowering effect can be achieved by concurrent administration of the compounds according to the invention with substances which bind bile acids, such as, for example, anion exchanger resins. The increased excretion of bile acids results in intensified de novo synthesis and thus in an increased breakdown of cholesterol (cf. M. S. Brown, P. T. Koranen and J. C. Goldstein, Science 212, 628 (1981); M. S. Brown, J. C. Goldstein, Spektrum der Wissenschaft 1, 96 (1985)).

The compounds of the formula I or II, according to the invention, can be used in the form of the δ-lactones, as free acids or in the form of their physiologically acceptable inorganic or organic salts, or as esters. Acids and salts or esters can be used in the form of their aqueous solutions or suspensions, or dissolved or suspended in pharmacologically acceptable organic solvents such as monohydric or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether or polyethers such as, for example, polyethylene glycol or in the presence of other pharmacologically acceptable polymeric vehicles such as, for example, polyvinylpyrrolidone, or in solid formulations.

The compounds of the formula I or II are preferably formulated in solid forms which can be administered orally and which may contain the customary auxiliaries. They are prepared by customary methods.

Particularly suitable formulations for oral use are tablets, coated tablets or capsules. One dosage unit preferably contains 10 to 500 mg of active substance.

EXAMPLE 1

Synthesis of methyl 3(RS),5(SR)-dihydroxy-7-[1-phenyl-2,5-dimethyl-4-(4-fluorophenyl)-1H-pyrrol-3-yl]hept-6(E)-enoate

[Formula I with AB=trans—HC═CH, $R^1$═$CH_3$, $R^2$═$CH_3$, $R^3$═phenyl, $R^4$═$CH_3$, $R^5$═p-fluorophenyl]

EXAMPLE 1.1

Ethyl 3-phenylaminobut-2(E)-enoate (ethyl N-phenylaminocrotonate) (Scheme 4 b)

A solution of 46.5 g (45.5 ml, 0.5 mol of aniline, 65 g (63.5 ml, 0.5 mol) of ethyl acetoacetate and 1 ml of glacial acetic acid in 100 ml of toluene was boiled under reflux with a water trap for 4 h. The solvent was removed by distillation in vacuo, and the residue was distilled under high vacuum.

57.9 g of colorless oil, boiling point 118°–120° C./1.5 torr.

MS: $C_{12}H_{15}NO_2$ (205), m/e=205 (M+).

EXAMPLE 1.2

1-(p-fluorophenyl)-2-nitropropene (Schemes 4 a and 4 b)

A solution of 84 g of p-fluorobenzaldehyde, 69.4 g of nitroethane and 4 ml of n-butylamine in 110 ml of xylene was boiled under reflux with a water trap for 20 h. On cooling to 0° C, 21.7 g of the product crystallized out, melting point 64°–5° C. This solid was filtered off with suction and washed with cold xylene.

41.4 g of nitroethane and 3 ml of n-butylamine were added to the filtrate, and the mixture was again boiled under reflux with a water trap for 14 h. The solvent was removed in vacuo, and the residue was triturated with methanol at 0° C., whereupon crystallization occurred. The solid was filtered off with suction and washed with cold methanol. 53.8 g, melting point 65°–66° C.

EXAMPLE 1.3

Ethyl 1-phenyl-2,5-dimethyl-4-(4-fluorophenyl)-1H-pyrrole-3-carboxylate

[Formula XVIII with $R^2 = CH_3$, $R^3 =$ phenyl, $R^4 = CH_3$, $R^5 =$ p-fluorophenyl, $R^{11} =$ ethyl]

A solution of 23.1 g (113 mmol) of ethyl N-phenylaminocrotonate (Example 1.1.) and 205 g (113 mmol) of the nitroolefin from Example 1.2. in 250 ml of ethanol was boiled under reflux for 30 h. The solvent was removed by distillation in vacuo, and the residue was chromatographed on 1 kg of silica gel using cyclohexane/ethyl acetate 95:5. 26 g of colorless oil.

$^1$H NMR (CDCl$_3$): $\delta = 1.05$ (t, 3H, ester CH$_3$), 1.85 (s, 3H, CH$_3$), 2.3 (s, 3H, CH$_3$), 4.1 (q, 2H, CH$_2$), 6.9–7.6 (m, 9H, arom. H).

MS: C$_{21}$H$_{20}$FNO$_2$ (337) m/e = 337 (M), 308, 292, 77.

EXAMPLE 1.4

Process step D2 (Scheme 3)

1-Phenyl-2,5-dimethyl-4-(4-fluorophenyl)-3-hydroxymethyl1H-pyrrole

Formula IV with $R^2 = CH_3$, $R^3 =$ phenyl, $R^4 = CH_3$, $R^5 =$ p-fluorophenyl]

A solution of 27.8 g of the ester from Example 1.3. in 300 ml of ether is added dropwise, at 5°–10° C., to a suspension of 7.8 g (0.2 mole) of lithium aluminum hydride in 300 ml of ether. The mixture is stirred at room temperature for 4 h and then, at 0° C., successive cautious dropwise additions of 35 ml of ethyl acetate, 16 ml of water and 24 ml of 2N sodium hydroxide solution are made. The mixture is stirred at room temperature for 30 min., the solid is filtered off with suction, and the filtrate is concentrated in vacuo. The residue is chromatographed on 1 kg of silica gel using cyclohexane/ethyl acetate 2:1 +0.2% triethylamine. 20.7 g of colorless oil which crystallizes very slowly.

$^1$H NMR(CDCl$_3$): $\delta = 1.3$ (s, broad, 1H, OH), 2.0 (s, 3H, CH$_3$), 2.1 (s, 3H, CH$_3$), 4.55 (s, 2H, CH$_2$), 6.9–7.65 (m, 9H, arom. H).

MS: C$_{19}$H$_{18}$FNO (295) m/e = 295 (M+), 278 (M+ —OH), 77.

EXAMPLE 1.5

Process step D3 (Scheme 3)
1-Phenyl-2,5-dimethyl-4-(4-fluorophenyl)-1H-pyrrole-3-carbaldehyde

[Formula III with $R^2 = CH_3$, $R^3 =$ phenyl, $R^4 = CH_3$, $R^5 =$ p-fluorophenyl]182.5 g of manganese dioxide are added twice, at at interval of 24 h, to a solution of 20.7 g of the alcohol from Example 1.4. in 1.2 liter of absolute ether and 12 ml of triethylamine. The mixture is stirred under N$_2$ a room temperature for 2 days, and the solid is filtered off with suction and washed with ether.

The filtrate is concentrated in vacuo, and the residue is chromatographed on silica gel using cyclohexane/ethyl acetate 6:1 +0.1 triethylamine. 13.2 g of yellowish solid.

huH NMR (CDCl$_3$): $\delta = 1.94$ (s, 3H, CH$_3$), 2.35 (s, 3H, CH$_3$), 6.95–7.7 (m, 9H, arom. H), 9.85 (s, 1H, CHO)
MS: C$_{19}$H$_{16}$FNO (293), m/e = 293 (M+), 77.

EXAMPLE 1.6

Process step Z1
3-[1-Phenyl-2,5-dimethyl-4-(4-fluorophenyl)-1H-pyrrol-3-yl]-(E)-propenal Formula XI with $R^2 = CH_3$, $R^3 =$ phenyl, $R^4 = CH_3$, $R^5 =$ p-fluorophenyl]

10 mmol of n-butyllithium (6.25 ml of a 1.6M solution in n-hexane) are added, at −70° C. under nitrogen, to a solution of 3.46 g (9.6 mmol) of 1-ethoxy-2-(tri-n-butylstannyl)ethylene (A. J. Leusink et al. J. Organomet. Chem. 9, 289 (1967)) in 110 ml of absolute THF. After 2 h at −73° C., a solution of 2.34 g (8 mmol) of the aldehyde from Example 1.5. in 12 ml of THF is added dropwise within 5 min. The interior temperature increases to −66° C. during this. The mixture is stirred at −73° C. for 2 h and at −50° C. for 10 min and then, at −40° C., 18.6 ml of a saturated aqueous ammonium chloride solution are added dropwise. The mixture is allowed to reach room temperature, the organic phase is separated off, the aqueous phase is extracted twice with ether, and the combined organic phases are washed with saturated brine (sodium chloride solution) and concentrated. The residue is taken up in 93 ml of THF, 18 ml of water and p-toluenesulfonic acid, and the mixture is stirred at room temperature for 1 h. The organic phase is separated off, and the aqueous phase is extracted with ether. The combined organic phases are washed with saturated brine, dried and concentrated. The residue is chromatographed on 450 g of silica gel using cyclohexane/ethyl acetate/triethylamine 3:1:0.1.

2.25 g of amorphous solid.

$^1$H NMR(CDCl$_3$): $\delta = 1.9$ (s, 3H, CH$_3$), 2.2 (s, 3H, CH$_3$), 6.07 (dd, 1H, =C—H), 6.9–7.7 (m, 10H, =C—H and 9 arom. H), 9.45 (d, 1H, CHO).

MS: C$_{21}$H$_{18}$FNO (319) m/e = 319 (M+), 290 (M+ —CHO), 77

EXAMPLE 1.7

Process step B1

Methyl 5(RS)-hydroxy-3-oxo-7-[1-phenyl-2,5-dimethyl-4-(4-fluorophenyl)-1H-pyrrol-3-yl]hept-6(E)-enoate

[Formula XII with $R^1 = CH_3$, $R^2 = CH_3$, $R^3 =$ phenyl, $R^4 = CH_3$, $R^5 =$ p-fluoropheny]

A solution of 1.43 g (12.33 mmol) of methyl acetoacetate in 10 ml of THF is added dropwise within 5 min to a suspension, at −15° C., of 12.7 mmol of sodium hydride (609 mg of a 50% suspension of NaH in mineral oil) in 86 ml of THF. The solution is stirred at −15° C. for 50 min. Then 7.68 ml (12.26 mmol) of a 1.6M solution of n-butyllithium in hexane is added dropwise within 10 min, and the mixture is then stirred at −15° C. for 20 min. At this temperature, a solution of 2.25 g (7.05 mmol) of the aldehyde from Example 1.6. in 25 ml of THF is added dropwise within 10 min, and the reaction solution is then stirred at −15° C. for 45 min. At −10° C., 13 ml of a saturated sodium dihydrogen phosphate solution are added dropwise. The reaction mixture is stirred at 0° C. for 5 min and is partitioned between ether and saturated brine. The organic phase is separated off, and the aqueous phase is extracted once with ether. The combined organic phases are washed with saturated brine, dried, filtered and concentrated. Silica gel chromatography using cyclohexane/ethyl acetate/triethylamine (2:1:0.1) provides 2.33 g of yellow oil.

¹H NMR(CDCl₃, 270 MHz): δ=1.6 (s, 1H, OH), 1.9 (s, 3H, CH₃), 2.13 (s, 3H, CH₃), 2.36 (s, 2H, CH₂), 3.57 (very narrow AB system 2H, CH₂), 3.73 (s, 3H, OCH₃), 5.99 (d, 1H, CH), 6.16 (dd, J=15.2 and 11.2 Hz, 1H, =C—H), 6.94 (d, J=15.2 Hz, 1H, =C—H), 7.08–7.33 (m, 5H, arom. H), 7.44–7.58 (m, 4H, arom. H).

MS: C₂₆H₂₆FNO₄ (435) m/e=435 (M+), 417 (M+—H₂O), 320, 319, 316, 290.

EXAMPLE 1.8

Process step B2

Methyl 3(RS),5(SR)-dihydroxy-7-[1-phenyl-2,5-dimethyl-4-(4-fluorophenyl)-1H-pyrrol-3-yl]hept-6(E)-enoate

[Formula I with AB=trans—CH=CH, R¹=CH₃, R²=CH₃, R³=phenyl, R⁴=CH₃, R⁵=p-fluorophenyl]

6.33 ml (6.33 mmol) of a 1M solution of triethylborane in THF are added dropwise within 5 min to a solution of 2.3 g (5.28 mmol) of the keto ester from Example 1.7. in 70 ml of absolute THF at 20° C. The mixture is stirred at room temperature for 20 min, and then 14.8 ml of dry air is introduced into the reaction solution within 5 min using a syringe. It is stirred a further 2 h at room temperature. The reaction mixture is cooled to −75° C., and 261 mg (6.864 mmol) of sodium borohydride are added in one portion. It is stirred at −75° C. for 12 h. At −10° C., 37 ml of saturated sodium dihydrogen phosphate solution are added dropwise. The reaction mixture is partitioned between ether and saturated brine. The organic phase is washed with brine, dried, filtered and concentrated. 370 ml of absolute methanol are added to the residue, and the mixture is stirred at room temperature for 3 h, then concentrated, and the residue is chromatographed on silica gel using cyclohexane/ethyl acetate/triethylamine 1:1:0.1. 1.9 g of pale yellow oil.

¹H NMR(C₆D₆, 270 MHz): δ=1.37 (dt, 1H, CH₂), 1.67 (dt, 1H, CH₂), 1.90 (s, 3H, CH₃), 2.08 (s 3H, CH₃), 2.05–about 2.12 (dd, overlap, 1H, CH₂), 2.26 (dd, 1H, CH₂), 2.40 (d, 1H, OH), 3.26 (s, 3H, OCH₃), 3.48 (d, 1H, OH), 4.11 (m, 1H, CH), 4.30 (m, 1H, CH), 5.72 (dd, J=16.0 and 6.0 Hz, 1H, =C—H), 6.72 (d, J=16.0 Hz, 1H, =C—H), 6.85–6.91 (m, 2H, arom. H), 6.95–7.17 (m, 5H, arom. H), 7.32–7.40 (m, 2H, arom. H).

MS: C₂₆H₂₈FNO₄ (437) m/e=437 (M+), 419 (M+—H₂O), 20, 302, 278

EXAMPLE 2

Process step A8 (Scheme 1)

Sodium 3(RS),5(SR)-dihydroxy-7-[1-phenyl-2,5-dimethyl-4-(4-fluorophenyl)-1H-pyrrol-3-yl]hept-6(E)-enoate

[Formula I with AB=trans-HC=CH, R¹=Na, R²=CH₃, R³=phenyl, R⁴=CH₃, R⁵=p-fluorophenyl]

3.45 ml of 1N sodium hydroxide solution are added, at 0° C., to a solution of 1.5 g (3.43 mmol) of the methyl ester from Example 1.8. in 100 ml of methanol, and the mixture is stirred for 2 h. The solvent is removed in vacuo, and 20 ml of methanol are added and again removed in vacuo. The residue is triturated with ether, decanting off, and again triturated with ether. This results in crystallization. Solvents are removed under high vacuum.

1.4 g of yellowish solid.

¹H NMR(D₂O, δHOD=4.8, 270 MHz): δ=1.6 (s, 3H, CH₃), 2.0 (s, 3H, CH₃), 2.1 (m, 2H, CH₂), 2.3 (m, 2H, CH₂), 3.97 (m, 1H, CH), 4.68 (d, 1H, CH), 5.62 (m, 2H, =CH), 6.8–7.4 (m, 9H, arom. H).

EXAMPLE 3

Process step A 9 (Scheme 1)

Methyl 3(RS),5(RS)-dihydroxy-7-[1-phenyl-2,5-dimethyl-4-(4-fluorophenyl)-1H-pyrrol-3-yl]heptanoate

[Formula I with AB=CH₂—CH₂, R¹=CH₃, R²=CH₃, R³=phenyl, R⁴=CH₃, R⁵=p-fluorophenyl]

About 50 mg of 10% palladium on charcoal are added to a solution of 75 mg of the ester from Example 1.8. in 20 ml of methanol and 0.1 ml of triethylamine, and the mixture is shaken for 10 min in a hydrogen atmosphere under normal pressure and at room temperature. The catalyst is filtered off and washed with methanol. The filtrate is concentrated in vacuo, and the residue is chromatographed on silica gel using toluene-/ethyl acetate/triethylamine 1:0.01.

47 mg of amorphous solid.

¹H NMR(C₆D₆, 270 MHz): δ=1.10 (dt, 1H, CH₂), 1.38 (dt, 1H, CH₂), 1.50–1.76 (m, 2H, CH₂), 1.97 (s, 3H, CH₃, 2.01 (dd, partial overlap, 1H, CH₂), 2.08 (s, 3H, CH₃), 2.17 (dd, 1H, CH₂), 2.77 (m, 2H, CH₂), 2.86 (d, 1H, OH), 3.27 (s, 3H, OCH₃), 3.50 (d, 1H, OH), 3.72 (m, 1H, CH), 3.95 (m, 1H, CH), 6.90–7.13 (m, 7H, arom. H), 7.28–7.36 (m, 2H, arom. H).

MS C₂₂H₃₀FNO₄ (439) m/e=439 (M+) 407 (M+—CH₃OH) 279, 278, 264, 118.

EXAMPLE 4

Process step A8 (Scheme 1)

Sodium 3(RS),5(RS)-dihydroxy-7-[1-phenyl-2,5-dimethyl-4-(4-fluorophenyl)-1H-pyrrol-3-yl]heptanoate

[Formula I with AB=CH₂—CH₂, R¹=Na, R²=CH₃, R³=phenyl, R⁴=CH₃, R⁵=p-fluorophenyl]

0.93 ml (0.093 mmol) of 0.1 N aqueous sodium hydroxide solution is added to a solution of 41 mg (0.093 mmol) of the ester from Example 3 in 10 ml of methanol at 0° C. After 90 min, the mixture is evaporated to dryness, and the powder is dried further under high vacuum. 42 mg of amorphous solid.

EXAMPLE 5

Synthesis of methyl 3(RS),5(SR)-dihydroxy-7-[1-phenyl-2-isopropyl-4-(4-fluorophenyl)-5-methyl-1H-pyrrol-3-yl]hept-(E)-enoate

[Formula I with AB=trans —CH=CH, R¹=CH₃, R²=isopropyl, R³=phenyl, R⁴=CH₃, R⁵=p-fluorophenyl]

EXAMPLE 5.1

3-Phenylamino-4-methylpent-2(E)-enanilide (Scheme 4 c)

A solution of 37 ml (0.41 mole) of aniline, 31 ml (0.2 mole) of ethyl 3-oxo-4-methylpentanoate and 1.0 ml of glacial acetic acid in 50 ml of toluene is boiled under reflux with a water trap for 6 hours. The solvent is removed in vacuo.

The residue crystallizes on cooling. Recrystallization from about 300 ml of hot toluene/petroleum ether (80°–110° C.) 2:1 (decanting hot) results in 38.7 g of colorless powder, melting point 147°–148° C. Further product can be obtained from the mother liquor.

¹H NMR(CDCl₃): δ=1.1 (d+m, 7H, C(CH₃)₂+amine H), 2.9 (sept., 1H, CH), 4.75 (s, 1H, =CH), 6.8–7.6 (m, 10H, arom. H), 11.1 (s, broad, 1H, amide H).

MS: $C_{18}H_{20}N_2O$ (280) m/e=280 (M+), 237 (M+ —CH(CH$_3$)$_2$), 188 (M+ —PhNH).

EXAMPLE 5.2

1-Phenyl-2-isopropyl-4-(4-fluorophenyl)-5-methyl-1H-pyrrole-3-carboxanilide

[Formula XIX with $R^2$=isopropyl, $R^3$=phenyl, $R^4$=CH$_3$, $R^5$=p-fluorophenyl, $R^{12}$=H]

A solution of 12.4 g (60 mmol) of 1-(p-fluorophenyl)-2-nitropropene (Example 1.2) and 17.1 g (61 mmol) of the anilide from Example 5.1 in 130 ml of ethanol is boiled under reflux and under nitrogen for 12 h. The ethanol is removed in vacuo, and the yellow solid residue is chromatographed on silica gel using cyclohexane/ethyl acetate 4:1. 19.7 g of yellow solid, melting point 186°-188° C. Recrystallization from cyclohexane/ethyl acetate yields a colorless solid of melting point 190°-192° C.

$^1$H NMR (CDCl$_3$): δ=1.3 (d, 6H, C(CH$_3$)$_2$), 1.83 (s, 3H CH$_3$), 3.2 (sept., 1H, CH), 6.8-7.6 (m, 15H, amide H +14 arom. H).

MS: $C_{27}H_{25}N_2OF$ (412) m/e=412 (M+), 320 (M+ —PhNH).

EXAMPLE 5.3

Process step D$_4$ (Scheme 3)

N-methylanilide of 1-phenyl-2-isopropyl-4-(4-fluorophenyl)-5-methyl-1H-pyrrole-3-carboxylic acid

[Formula XX with $R^2$=isopropyl, $R^3$=phenyl, $R^4$=CH$_3$, $R^5$=p-fluorophenyl, $R^{12}$=H]

1.2 g of 50% sodium hydride/mineral oil are added in portions, with mechanical stirring, under nitrogen to a solution of 4.5 g of the anilide from Example 5.2 in 50 ml of toluene.

The mixture is heated at 60° C. for 30 min and at 110° C. for 10 min. It is cooled to 30° C., and 5.8 ml of methyl iodide are added in one portion. The mixture is then boiled under reflux with a bath temperature of 75° C. for 16 h. The mixture is cooled with methanol/dry ice, and 16 ml of water are slowly added dropwise. The temperature is allowed to rise to 5° C., about 200 ml of ether are added, and the organic phase is separated off, washed with saturated brine, dried and concentrated in vacuo. The residue crystallizes on trituration with n-hexane. 3.9 g of pale yellow solid, melting point 60°-63° C.

$^1$H NMR (CDCl$_3$): δ=1.2 (d, 3H, CH$_3$), 1.3 (d, 3H, CH$_3$), 1.8 (s, 3H CH$_3$). 2.8 (sept 1H CH) 3 17 (s 3H. N—CH$_3$), 6.5-7.5 (m, 14H, arom. H).

MS: $C_{28}H_{27}N_2OF$ (426) m/e=426 (M+), 320 (M+ —PhNCH$_3$).

EXAMPLE 5.4

Process step D$_5$ (Scheme 3)

1-Phenyl-2-isopropyl-3-hydroxymethyl-4-(4-fluorophenyl)-5-methyl-1H-pyrrole

[Formula IV with $R^2$=isopropyl, $R^3$=phenyl, $R^4$=CH$_3$, $R^5$=p-fluorophenyl]

A solution of 3.83 g (9 mmol) of the N-methylanilide from Example 5.3. in 30 ml of THF are added to a suspension of 1.02 g (27 mmol) of LiAlH$_4$ in 40 ml of absolute THF. The mixture is boiled under reflux and under nitrogen for 18 h. At 0° C., successive dropwise additions of 5 ml of ethyl acetate, 2 ml of water and 3 ml of 2N sodium hydroxide solution are made, and the mixture is stirred at room temperature for 30 min. The solid is filtered off with suction, and the filtrate is concentrated in vacuo. The residue is triturated with pentane, whereupon the product crystallizes. The pentane mother liquor contains the byproduct N-methylaniline.

Alternatively, the crude product can be filtered through silica gel using toluene/ethyl acetate 20:1+1% triethylamine. 1.82 g of colorless solid.

$^1$H NMR (CDCl$_3$): δ=1.25 (d, 6H, C(CH$_3$)$_2$), 1.9 (s, 3H, CH$_3$), 2.8 (m, 1H, CH), 4.35 (s, 1H, OH), 4.55 (s, 2H, CH$_2$), 6.85-7.75 (m, 9H, arom. H).

MS: $C_{21}H_{22}NOF$ (323) m/e=323 (M+), 308 (M+ —CH$_3$), 290 (M+ —CH$_3$—H$_2$O).

EXAMPLE 5.5

Process step D$_3$ (Scheme 3)

1-Phenyl-2-isopropyl-4-(4-fluorophenyl)-5-methyl-1H-pyrrole-3-carbaldehyde

[Formula III with $R^2$=isopropyl, $R^3$=phenyl, $R^4$=CH$_3$, R5=p-fluorophenyl]

A solution of 7.9 g (100 mmol) of absolute pyridine in 50 ml of methylene chloride is added dropwise, at 15°-20° C., to a suspension of 10 g of Celite and 5 g (50 mmol) of finely powdered chromium trioxide in 100 ml of absolute methylene chloride. The mixture is stirred at room temperature for 20 min, and a solution of 1.61 g (5 mmol) of the alcohol from Example 5.4 in 50 ml of methylene chloride is rapidly added dropwise. The mixture is stirred at room temperature for 45 min and rapidly filtered with suction through a elite filter. The solid is thoroughly washed with methylene chloride, and the combined filtrates are concentrated in vacuo. The residue is taken up in cyclohexane/ethyl acetate/triethylamine 1:1:0.01, and the mixture is again filtered with suction through a Celite filter. The solid is thoroughly washed, and the combined filtrates are concentrated in vacuo. The residue is chromatographed on 800 g of silica gel using cyclohexane/ethyl acetate/triethylamine 3:1:0.01. 720 mg of yellowish solid.

$^1$H NMR CDCl$_3$: δ=1.3 (d, 6H, C(CH$_3$)$_2$), 2.1 (s, 3H, CH$_3$), 3.1 (sept., 1H, CH), 6.9-7.6 (m, 9H, arom. H), 10.0 (s, 1H, CHO).

MS: $C_{21}H_{20}NOF$ (321) m/e=321 (M+).

EXAMPLE 5.6

Process step Z1

3-[1-Phenyl-2-isopropyl-4-(4-fluorophenyl)-5-methyl-1H-pyrrol-3-yl]-(E)-propenal

[Formula XI with $R^2$=isopropyl, $R^3$=phenyl, $R^4$=CH$_3$, $R^5$=p-fluorophenyl]

In analogy to Example 1.6, 686 mg of yellowish solid are obtained from 700 mg of the aldehyde from Example 5.5. $^1$H NMR (CDCl$_3$): δ=1.3 (d, 6H, C(CH$_3$)$_2$), 2.0 (s, 3H, CH$_3$), 3.1 (sept., 1H, CH), 6.1 (dd, J=16 and 8Hz, 1H, =C—H), 7.0-7.8 (m, 10H, =C—H and 9 arom. H), 9.5 (d, J=8 Hz, 1H, CHO).

MS: $C_{23}H_{22}NOF$ (347) DCI m/e=348.2 (M+H+).

EXAMPLE 5.7

Process step B1

Methyl 5(RS)-hydroxy-3-oxo-7-[1-phenyl-3-isopropyl-4-(4-fluorophenyl)-5-methyl-1H-pyrrol-3-yl]hept-6(E)-enoate

[Formula XII with $R^1$=CH$_3$, $R^2$=isopropyl, $R^3$=phenyl, $R^4$=CH$_3$, $R^5$=p-fluorophenyl]

In analogy to Example 1.7, 672 mg of yellow oil are obtained from 660 mg of the aldehyde from Example 5.6.

MS: $C_{28}H_{30}FNO_4$ (463) m/e=463 (M+), 446 (M+—OH).

EXAMPLE 5.8

Process step B2

Methyl 3(RS),5(SR)-dihydroxy-7-[1-phenyl-2-isopropyl-4-(4-fluorophenyl)-5-methyl-1H-pyrrol-3-yl]hept-6(E)-enoate

[Formula I with AB=trans-HC=CH, $R^1$=CH$_3$, $R^2$=isopropyl, $R^3$=phenyl, $R^4$=CH$_3$, $R^5$=p-fluorophenyl]

In analogy to Example 1.8., 605 mg of pale yellow viscous oil are obtained from 640 mg of the keto ester from

EXAMPLE 5.7

$^1$H NMR (C$_6$D$_6$): δ=1.3 (d+m, 7H, C(CH$_3$)$_2$ and CH$_2$), 1.6 (m, 1H, CH$_2$), 1.95 (s, 3H, CH$_3$), 2.0-2.3 (m, 2H, CH$_2$), 2.5 (s, br., 1H, OH), 3.1 (sept., 1H, CH), 3.3 (s, 3H, OCH$_3$), 3.5 (s, broad, 1H, OH), 4.1 (m, 1H, CH), 4.3 (m, 1H, CH), 5.7 (dd, J=16 and 6 Hz, 1H, =C—H), 6.8-7.5 (m, 10H, =C—H and 9 arom. H).

MS: $C_{28}H_{32}FNO_4$ (465) m/e=465 (M+), 447 M+ —H$_2$O)

EXAMPLE 6

Process step A8 (Scheme 1)

Sodium 3(RS),5(SR)-dihydroxy-7-[1-phenyl-2-isopropyl-4-(4-fluorophenyl)-5-methyl-1H-pyrrol-3-yl]hept-6(E)-enoate

[Formula I with AB=trans-HC—CH, $R^1$=Na, $R^2$=isopropy, $R^3$=phenyl, $R^4$=CH$_3$, $R^5$=p-fluorophenyl]is obtained from the product of Example 5.8 in analogy to Example 2.

EXAMPLE 7

Process step A9 (Scheme 1)

Methyl 3(RS),5(RS)-dihydroxy-7-[1-phenyl-2-isopropyl-4-(4-fluorophenyl)-5-methyl-1H-pyrrol-3-yl]heptanoate

[Formula I with AB=CH$_2$—CH$_2$, $R^1$ CH$_3$, $R^2$=isopropyl, $R^3$=phenyl, $R^4$=CH$_3$, $R^5$=p-fluorophenyl]is obtained from the product of Example 5.8 in analogy to Example 3.

$^1$H NMR (C$_6$D$_6$): δ=1.1-1.5 (m, 2H, CH$_2$), 1.3 (d, 6H, C(CH$_3$)$_2$), 1.6-2.2 (m+s, 7H, 2×CH$_2$ and CH$_3$), 2.9-3.2 (m, 4H, CH$_2$, CH and OH), 3.3 (s, 3H, OCH$_3$), 3.45 (s, broad, 1H, OH), 3.8-4.1 (m, 2H, 2×CH), 6.8-7.5 (m, 9H, arom. H)

MS: $C_{28}H_{34}FNO_4$ (467) FAB m/e=468 (M+H+).

EXAMPLE 8

Process step A8 (Scheme 1)

Sodium 3(RS),5(RS)-dihydroxy-7-[1-phenyl-2-isopropyl-4-(4-fluorophenyl)-5-methyl-1H-pyrrol-3-yl]heptanoate

[Formula I with AB=CH$_2$—CH$_2$, $R^1$=Na, $R^2$=isopropyl, $R^3$=phenyl, $R^4$=CH$_3$, $R^5$=p-fluorophenyl]is obtained from the product of Example 7 in analogy to Example 4.

EXAMPLE 9

Synthesis of methyl 3(RS),5(SR)-dihydroxy-7-[1-phenyl-2-methyl-4-(4-fluorophenyl)-1H-pyrrol-3-yl]hept-6(E)-enoate

[Formula I with AB=trans-HC=CH, $R^1$=CH$_3$, $R^2$=CH$_3$, $R^3$=phenyl, $R^4$=H, $R^5$=p-fluorophenyl]

EXAMPLE 9.1.

N,N-bis 3-(4-fluorophenyl)-4-methoxycarbonyl-5-methyl-2,3-dihydrofuran-2-yl]hydroxylamine (Scheme 4 a)

20.9 g (180 mmol) of methyl acetoacetate are added, at 0° C., to a stirred solution of 2.92 g (54 mmol) of sodium methanolate in 54 ml of methanol, followed by 30.1 g (180 mmol) of 4-fluoro-β-nitrostyrene (1-p-fluorophenyl-2-nitroethylene, prepared as described in GattermannWieland "Die Praxis des organischen Chemikers" (Organic Chemical Practice) 43rd Edition, W. de Gruyter Berlin 1982, page 361) in portions. Stirring at 0° C. for 15 min results in a thick paste which is left to stand at 0° C. for 2 h. The precipitate is filtered off with suction, washed with ice-cold methanol and dried in vacuo over phosphorus pentoxide. 22.0 g of colorless solid, melting point 135°-137° C. The mother liquor is concentrated to about 75 ml. The product which has crystallized out is filtered off with suction, washed and dried. 7.0 g of colorless solid, melting point 139°-141° C.

$^1$H NMR (DMSO-d$_6$ : =2.25 s, 6H, 2×C—CH$_3$), 3.32 (s, 3H, OCH$_3$), 3.50 (s, 3H, OCH$_3$), 4.30 (dd, 2H, CH), 5.40 (d, 2H, CH), 7.16 (d, 8H, arom. H), 8.72 (s, 1H, OH).

MS: $C_{26}H_{25}F_2NO_7$ (501) FAB m/e=502 (M+H+), 458, 235.

EXAMPLE 9.2.

1-Phenyl-2-methyl-3-methoxycarbonyl-4-(p-fluorophenyl)-1H-pyrrole

[Formula XVIII with $R^2$=CH$_3$, $R^3$=phenyl, $R^4$=H, $R^5$=p-fluorophenyl, $R^{11}$=CH$_3$]

5.59 g (60 mmol) of aniline are added to a solution of 15.05 g (30 mmol) of the hydroxylamine from Example 9.1 in 600 ml of ethanol, and the mixture is then boiled under reflux for 24 h. Since TLC shows not only products but also about 20% starting material, a further 1.1 g of aniline are added, and the mixture is boiled for a further 16 h. The solvent is removed by distillation in vacuo, and the residue is partitioned between dichloromethane and 1N hydrochloric acid. The organic phase is washed with saturated sodium bicarbonate solution and then with brine, dried, filtered and concentrated. The residue is chromatographed on silica gel using n-hexane/diethyl ether/dichloromethane 16:3.5:0.5. 4.0 g of red-brown syrup.

$^1$H NMR (CDCl$_3$): δ=2.43 (s, 3H, CH$_3$), 3.70 (s, 3H, OCH$_3$), 6.70 (s, 1H, arom. H), 6.87-7.66 (m, 9H, arom. H)

MS: $C_{19}H_{16}FNO_2$ (309) m/e=309 (M$^{30}$), 278, 248.

EXAMPLE 9.3

Process step D$_2$ (Scheme 3)

1-Phenyl-2-methyl-3-hydroxymethyl-4-(p-fluorophenyl)-1H-pyrrole

[Formula IV with $R^2$=CH$_3$.$R^3$=phenyl, $R^4$=H, $R^5$=p-fluorophenyl]

A solution of 3.68 g (11.9 mmol) of the methyl ester from Example 9 in 75 ml of ether is added within 5 min, at 0° C., to a suspension of 1.13 g (29.75 mmol) of lithium aluminum hydride in 150 ml of dry ether. The mixture is stirred at 0° C. for 1 hour and then, at this temperature, successive dropwise additions of 10 ml of ethyl acetate, 2.5 ml of water and 5 ml of 2N sodium hydroxide solution are made. The mixture is stirred for 15 min, the inorganic precipitate is filtered off with suction, and 2 ml of triethylamine are added to the filtrate which is then concentrated in vacuo. The residue is chromatographed on silica gel using cyclohexane/ethyl acetate 5:2+0.1% triethylamine.

3.2 g of pale yellow viscous resin.

$^1$H NMR (CDCl$_3$):$\delta$=1.5 (broad, 1H, OH), 2.26 (s, 3H, CH$_3$), 4.63 (s, 2H, CH$_2$), 6.87 (s, 1H, arom..H), 6.93–7.70 (m, 9H, arom. H).

MS: C$_{18}$H$_{16}$FNO (281) m/e=281 (M+), 264 (M+—OH), 77.

EXAMPLE 9.4

Process step D$_3$ (Scheme 3)

1-Phenyl-2-methyl-4-(p-fluorophenyl)-1H-pyrrole-3-carboxaldehyde

[Formula III with R$^2$=CH$_3$, R$^3$=phenyl, R$^4$=H, R$^5$=p-fluorophenyl]

In analogy to Example 1.5. 2.38 g of yellowish viscous resin are obtained from 3.2 g of the alcohol from Example 9.3.

$^1$H NMR (CDCl$_3$): $\delta$=2.50 ( 3H CH$_3$) 6.80 (s, 1H, arom. H) 6.85–7.70 (m, 9H, arom. H), 10.03 (s, 1H, CHO)

MS: C$_{18}$H$_{14}$FNO (279.3) m/e=279 (M+), 278 (M+—H).

EXAMPLE 9.5

Process step Z1

3-[1-Phenyl-2-methyl-4-(p-fluorophenyl)-1H-pyrrol-3-yl]-(E)-propenal

[Formula XI with R$^2$=CH$_3$, R$^3$=phenyl, R$^4$=H, R$^5$=p-fluorophenyl]

In analogy to Example 1.6, 1.98 g of pale yellow crystals are obtained from 1.8 g of the aldehyde from Example 9.4. $^1$H NMR (CDCl$_3$): $\delta$2.36 (s, 3H, CH$_3$), 6.26 (dd, J=16.0 and 7.8 Hz, 1H, =C—H), 6.97 (d, J=16.0 Hz, 1H, =C—H), 7.15–7.70 (m, 10H, arom. H), 9.54 (d, J=7.8 Hz, 1H, CHO) MS C$_{20}$H$_{16}$FNO (305) m/e=305 (M+), 290, 276, 264.

Alternative Process step Z2

β-[1-Phenyl-2-methyl-4-(p-fluorophenyl)-1H-pyrrol-3-yl-]-(E)-acrylonitrile

[Formula XVII with R$^2$=CH$_3$, R$^3$=phenyl, R$^4$=H, R$^5$=p-fluorophenyl]

A solution of 135 mg (0.66 mmol) of diisopropyl cyanomethylphosphonate in 2 ml of THF is added dropwise, at 0° C., to a suspension of 37.8 mg of 50% sodium hydride/mineral oil (0.787 mmol) in 7 ml of absolute THF. The mixture is stirred at 0° C. for 40 min, and then a solution of 122 mg (0.437 mmol) of the aldehyde from Example 9.4 in 5 ml of THF is added dropwise. The mixture is stirred at 0° C. for 5 min and at room temperature for 2 h.

The reaction mixture is poured into aqueous brine, the mixture is extracted with ether, and the ethereal extract is washed with brine, then dried, filtered and concentrated. The residue is chromatographed on silica gel using cyclohexane/ethyl acetate 6:1+0.1% triethylamine.

103 mg of pale yellow resinous solid.

$^1$H NMR CDCl$_3$: $\delta$=2.30 (s, 3H, CH$_3$), 5.23 (d. J=17 Hz, 1H, =C—H), 6.73 (s, 1H, arom. H), 7.0–7.6 (m, 10H, =C—H and 9 arom. H).

MS: C$_{20}$H$_{15}$FN$_2$ (302) m/e=302 (M+), 77.

Process step Z3

0.6 ml of a 1.2M solution of diisobutylaluminum hydride in toluene (0.72 mmol) is added dropwise, at 0° C., to a solution of 72.4 mg (0.24 mmol) of the above nitrile in 5 ml of absolute THF. The mixture is stirred at 0° C. for 1 h and at room temperature for 1.5 h and, at 0° C., 1 ml of saturated sodium dihydrogen phosphate solution is cautiously added dropwise, followed by 2 ml of water. The mixture is stirred at 0° C. for 30 min and at room temperature for 1 h. Saturated brine is added to the reaction mixture which is then extracted twice with ether. The combined organic phases are washed with NaHCO$_3$-solution, dried, filtered and concentrated. The residue is chromatographed on silica gel using cyclohexane/ethyl acetate 5:1+0.1% triethylamine. 50.5 mg of pale yellow crystals whose spectra are identical to the above material from process step Z1 described in Example 9.5.

EXAMPLE 9.6

Process step B1

Methyl 5(RS)-hydroxy-3-oxo-7-[1-phenyl-2-methyl-4-(p-fluorophenyl)-1H-pyrrol-3-yl]hept-6(E)-enoate

[Formula XII with R$^1$=CH$_3$, R$^2$=CH$_3$, R$^3$=phenyl, R$^4$=H, R$^5$=p-fluorophenyl]

In analogy to Example 1.7, 321 mg of pale yellow oil are obtained from 292 mg of the aldehyde from Example 9.5.

$^1$H NMR (CDCl$_3$, 270 MHz): $\delta$=2.27 (s, 3H, CH$_3$), 2.55 (broad, 1H, OH), 2.80 (m, 2H, CH$_2$), 3.50 (s, 2H, CH$_2$), 3.74 (s, 3H, OCH$_3$), 4.69 (q, 1H, CH), 5.65 (dd, J=16.0 and 6.8 Hz, 1H, =C—H), 6.60 (d, J=16.0 Hz, 1H, =C—H), 6.76 (s, 1H, arom. H), 7.00–7.12 (m, 4H, arom. H), 7.30–7.52 (m, 5H, arom. H).

MS: C$_{25}$H$_{24}$FNO$_4$ (421.4) m/e=421 M+), 403 (M+ —H$_2$O), 345, 302, 77.

EXAMPLE 9.7

Process step B2

Methyl 3(RS),5(SR)-dihydroxy-7-[1-phenyl-2-methyl-4-(p-fluorophenyl)-1H-pyrrol-3-yl]hept-6(E)-enoate

[Formula I with AB=trans-HC=CH, R$^1$=CH$_3$, R$^2$=CH$_3$, R$^3$=phenyl, R$^4$=H, R$^5$=p-fluorophenyl]

In analogy to Example 1.8, 107 mg of pale yellow viscous oil are obtained from 303 mg of the keto ester from Example 9.6.

$^1$H NMR (CDCl$_3$, 270 MHz): $\delta$=2.12 (m, 2H, CH$_2$), 2.24 (s, 3H, CH$_3$), 2.37 (s, 2H, 2×OH), 2.54 (dd, 1H, CH$_2$), 2.75 (dd, 1H, CH$_2$), 3.72 (OCH$_3$), 4.26 (m, 1H, CH), 5.32 (m, 1H, CH), 5.75–5.85 (m, 2H, =C—H), 6.78 (s, 1H, arom. H), 7.00–7.10 (m, 2H, arom. H), 7.28–7.50 (m, 7H, arom. H).

MS: C$_{25}$H$_{26}$FNO$_4$ (423) m/e=423 (M+)+, 306, 264.

EXAMPLE 10

Process step A8 (Scheme 1)

Sodium 3(RS),5(SR)-dihydroxy-7-[1-phenyl-2-methyl-4-p-fluorophenyl)-1H-pyrrol-3-yl]hept-6(E)-enoate

[Formula I with AB=trans -HC=CH, R$^1$=Na, R$^2$=CH$_3$, R$^3$=phenyl, R$^4$=H, R$^5$=p-fluorophenyl]

3.2 ml of 0.1 N sodium hydroxide solution and, after one hour, a further 0.3 ml of 0.1 N sodium hydroxide solution are added to a solution of 131 mg (0.31 mmol) of the ester from Example 9.7 in 15 ml of methanol.

After a further 30 min, the solvent is removed by distillation in vacuo, the residue is dissolved in 30 ml of water, and the aqueous solution is washed once with pentane/ether (1:1). The aqueous phase is filtered and freeze-dried, resulting in 149 mg of colorless powder, melting point 180° C., decomposition at 222°-223° C.

TLC: chloroform/methanol 7:3+0,1% triethylamine: methyl ester $R_f$=0.78, product: $R_f$=0.28.

EXAMPLE 11

Synthesis of methyl 3(RS),5(SR)-dihydroxy-7-[1-phenyl-2-isopropyl-4-(4-fluorophenyl)-1H-pyrrol-3-yl]hept-6(E)-enoate

[Formula I with AB=trans —CH=CH, $R^1$=CH$_3$, $R^2$=isopropyl, $R^3$=phenyl, $R^4$=H, $R^5$=p-fluorophenyl]

EXAMPLE 11.1

1-Phenyl-2-isopropyl-4-(4-fluorophenyl)-1H-pyrrole-3-carboxanilide (Scheme 4 c)

A solution of 12.5 g (75 mmol) of 1-p-fluorophenyl-2nitroethylene (Gattermann-Wieland, 43rd Edition, page 361) and 23.1 g (82.5 mmol) of 3-phenylamino-4-methyl-pent-2(E)-enanilide (Example 5.1.) in 200 ml of ethanol boiled under reflux for 18 h. The solvent is removed in vacuo, and the residue is taken up in a little cyclohexane/ethyl acetate 9:1+1% NEt$_3$. This results in a large part of the reaction product not dissolving. The solid is filtered off with suction and recrystallized from methanol. 11.94 g of colorless solid, melting point 192°-194° C.

The above filtrate is chromatographed on silica gel using the same solvent and yields a further 2.8 g of the product. $^1$H NMR (CD$_2$Cl$_2$): $\delta$=1.30 (d, 6H, C(CH$_3$)$_2$), 3.14 (sept., 1H, CH), 6.73 (s, 1H, arom. H), 7.00-7.70 (m, 10H, amide H and 9 arom. H)

EXAMPLE 11.2

Process step D4

N-methylanilide of 1-phenyl-2-isopropyl-4-(4-fluorophenyl)-1H-pyrrole-3-carboxylic acid

[Formula XX with $R^2$=isopropyl, $R^3$=phenyl, $R^4$=H, $R^5$=p-fluorophenyl, $R^{12}$=H]

In analogy to Example 5.3, 14.5 g of colorless solid, melting point 126°-127° C., are obtained from 14.4 g of the anilide from Example 11.1 after chromatography on silica gel using cyclohexane/ethyl acetate/triethylamine 8:2:0.01.

MS: C$_{27}$H$_{25}$FN$_2$O (412) m/e=412 (M+), 306, 262.

EXAMPLE 11.3

Process step D$_5$ (Scheme 3)

1-Phenyl-2-isopropyl-3-hydroxymethyl-4-(4-fluorophenyl)-1H-pyrrole

[Formula IV with $R^2$=isopropyl, $R^3$=phenyl, $R^4$=H, $R^5$=p-fluorophenyl]

In analogy to Example 5.4, 10.4 g of viscous colorless oil are obtained from 14.5 g of the N-methylanilide from Example 11.2.

$^1$H NMR (CDCl$_3$): $\delta$=1.28 (d, 7H, C(CH$_3$)$_2$+OH), 3.03 (sept., 1H, CH), 4.70 (s, 2H, CH$_2$), 6.73 (s, 1H, arom. H), 6.90-7.70 (m, 9H, arom. H).

MS: C$_{20}$H$_{20}$FNO.(309) m/e=309 (M+), 294, 276, 77.

EXAMPLE 11.4

Process step D$_3$ (Scheme 3)

1-Phenyl-2-isopropyl-4-(4-fluorophenyl)-1H-pyrrole-3-carbaldehyde

[Formula III with $R^2$=isopropyl, $R^3$=phenyl, $R^4$=H, $R^5$=p-fluorophenyl]

A solution of 40.9 g (0.517 mole) of pyridine in 50 ml of absolute methylene chloride is added, at 15°-20° C. under nitrogen, to a suspension of 25.9 g (0.258 mole) of finely powdered chromium trioxide and 15 g of Celite in 250 ml of absolute methylene chloride. The mixture is stirred at room temperature for 20 min and then a solution of 8 g (25.8 mmol) of the alcohol from Example 11.3. in 150 ml of absolute methylene chloride is added dropwise very rapidly. The interior temperature is maintained between 20° and 24° C. by cooling in ice. After 15 min, 500 ml of cyclohexane are added, and the mixture is filtered with suction through a Celite filter, washing with methylene chloride/cyclohexane 3:7. The filtrate is concentrated, and the residue in the flask is taken up in cyclohexane/ ethyl acetate 6:4 and again filtered with suction through a Celite filter. The solid is then thoroughly washed, the filtrate is concentrated, and the residue in the flask is chromatographed on 500 g of silica gel using cyclohexane/ ethyl acetate 4:1.

2.4 g of yellowish oil which slowly crystallizes.

ALTERNATIVE PROCEDURE 3.8 g (4.0 mmol) of tris(triphenylphosphine)ruthenium(II) dichloride are added to a solution of 46.8 g (400 mmol) of N-methylmorpholine N-oxide in 400 ml of acetone (dried over K$_2$CO$_3$). The mixture is stirred at 20° C. for 20 min. A solution of the alcohol from Example 11.3. (30.9 g, 100 mmol) in 600 ml of dry acetone is added dropwise, and the reaction mixture is stirred at room temperature for 20 h. It is filtered through a short, thick layer of silica gel (about 500 g), washing with 3 liters of ether. The filtrate is concentrated in vacuo, and the residue is chromatographed on 800 g of silica gel using cyclohexane/ethyl acetate/triethylamine 4:1:0.1. 26.6 g (87% yield) of pale yellow crystals, melting point 119°-120° C.

$^1$H NMR (CDCl$_3$): $\delta$=1.36 (d, 6H, C(CH$_3$)$_2$), 3.16 (sept., 1H, CH), 6.65 (s, 1H, arom. H), 7.0-7.7 (m, 9H, arom. H), 10.1 (s, 1H, CHO).

MS C$_{20}$H$_{18}$FNO (307) m/e=307 (M+), 292, 77.

EXAMPLE 11.5

Process step Z1

3-[1-Phenyl-2-isopropyl-4-(4-fluorophenyl)-1H-pyrrol-3-yl]-(E)-propenal

[Formula XI with $R^2$=isopropyl, $R^3$=phenyl, $R^4$=H, $R^5$=p-fluorophenyl]

In analogy to Example 1.6, 1.3 g of the product are obtained as an oil, which slowly crystallizes, in addition to 1.1 g of unreacted starting material, from 2.4 g of the aldehyde from Example 11.4. It should be possible to achieve quantitative reaction by increasing the reaction time and (or) a somewhat higher reaction temperature.

$^1$H NMR (CDCl$_3$): $\delta$=1.35 (d, 6H, C(CH$_3$)$_2$), 3.16 (sept. 1H, CH), 6.05 (dd, J=16 Hz and 7.6 Hz, 1H, =CH), 6.63 (s, 1H, arom. H), 7.0-7.5 (m, 9H, arom. H), 7.75 (d, J=16 Hz, 1H, =CH), 9.50 (d, J=7.6 Hz, 1H, CHO)

MS: C$_{22}$H$_{20}$FNO (333) DCI m/e=334.2 (M+H+), 290.2.

EXAMPLE 11.6

Process step B1

Methyl 5(RS)-hydroxy-3-oxo-7-[1-phenyl-2-isopropyl-4-(4-fluorophenyl)-1H-pyrrol-3-yl]hept-6(E)-enoate

[Formula XII with $R^1=CH_3$, $R^2$=isopropyl, $R^3$=phenyl, $R^4$=H, $R^5$=p-fluorophenyl]

In analogy to Example 1.7, 1.4 g of the product (oil) are obtained from 1.3 g of the aldehyde from Example 11.5.

MS: $C_{27}H_{28}FNO_4$ (449) m/e=449 (M+), 432 (M+—OH), 373, 334, 290.

EXAMPLE 11.7

Process step B2

Methyl 3(RS),5(SR)-dihydroxy-7-[1-phenyl-2-isopropyl-4-(4-fluorophenyl)-1H-pyrrol-3-yl]hept-6(E)-enoate

[Formula I with AB=trans-HC=CH, $R^1=CH_3$, $R^2$=isopropyl, $R^3$=phenyl, $R^4$=H, $R^5$=p-fluorophenyl]

In analogy to Example 1.8, 1.28 g of product (viscous oil) are obtained from 1.4 g of the 8-keto ester from Example 11.6.

$^1$H NMR ($C_6D_6$): =1.30 (d+m, 7H, $C(CH_3)_2$, and $CH_2$) 1.57 (dt, 1H, $CH_2$), 2.03 (dd, 1H, $CH_2$), 2.18 (dd, 1H, $CH_2$), 2.70 (s, broad, 1H, OH), 3.09 (sept., 1H, CH), 3.27 (s, 3H, $OCH_3$), 3.45 (s, broad, 1H, OH), 4.03 (m, 1H, CH), 4.34 (m, 1H, CH), 5.67 (dd, J=16 and 6 Hz, 1H, =CH), 6.50 (s, 1H, arom. H), 6.87–7.15 (m, 8H, =CH and 7 arom. H), 7.45 (dd, 2H, arom. H).

MS: $C_{27}H_{30}FNO_4$ (451) m/e=451 (M+), 433M+—$H_2O$), 334 292, 290, 276.

EXAMPLE 12

Process step A8 (Scheme 1)

Sodium 3(RS),5(SR)-dihydroxy-7-[1-phenyl-2-isopropyl-4-(4-fluorophenyl)-1H-pyrrol-3-yl]hept-6(E)-enoate

[Formula I with AB=trans-HC=CH, $R^1$=Na, $R^2$=isopropyl, $R^3$=phenyl, $R^4$=H, $R^5$=p-fluorophenyl]is obtained from the product of Example 11.7. in analogy to Example 2.

EXAMPLE 13

Process step A9 (Scheme 1)

Methyl 3(RS),5(RS)-dihydroxy-7-[1-phenyl-2-isopropyl-4(4-fluorophenyl)-1H-pyrrol-3-yl]heptanoate

[Formula I with AB=$CH_2$—$CH_2$, $R^1=CH_3$, $R^2$=isopropyl, $R^3$=phenyl, $R^4$=H, $R^5$=p-fluorophenyl]is obtained from the product of Example 11.7. in analogy to Example 3.

$^1$H NMR $C_6D_6$, 270 MHz):δ=1.03 (dt, 1H, $CH_2$), 1.28–1.43 (m, partial overlap, 1H, $CH_2$), 1.32 (d, 3H, $CH_3$), 1.33 (d, H, $CH_3$, 1.60–1.85 (m, 2H, $CH_2$), 1.94 (dd, 1H, $CH_2$), 2.12 (dd, 1H, $CH_2$), 2.90–3.02 (m, 1H, $CH_2$), 3.03–3.22 (m, 3H, $CH_2$, CH, 1 OH , 3.24 (s, 3H, $OCH_3$), 3.43 (s, broad, 1H, 1 OH), 3.75 (m, 1H, CH), 3.88 (m, 1H, CH), 6.58 (s, 1H, arom. H), 6.94 (AA'BB', 2H, arom. H), 7.03–7.15 (m, 5H, arom. H), 7.42 (AA'BB', 2H, arom. H).

MS: $C_{27}H_{32}FNO_4$ (453) FAB m/e=454 (M+H ), 292.

EXAMPLE 14

Process step A8 (Scheme 1)

Sodium 3(RS),5(RS)-dihydroxy-7-[1-phenyl-2-isopropyl-4-(4-fluorophenyl)-1H-pyrrol-3-yl]heptanoate

[Formula I with AB=$CH_2$—$CH_2$, $R^1$=Na, $R^2$=isopropyl, $R^3$=phenyl, $R^4$=H, $R^5$=p-fluorophenyl]is obtained from the product of Example 13 in analogy to Example 2, melting point 230°–233° C. (decomposition).

EXAMPLE 15

Synthesis of methyl 3(RS),5(SR)-dihydroxy-7-[1-isopropyl-2-methyl-4-(4-fluorophenyl)-1H-pyrrol-3-yl]hept-6(E)-enoate a I with AB=trans-HC=CH, $R^1=CH_3$, $R^2=CH_3$,

[Formula I with AB=trans-HC=CH, $R^1=CH_3$, $R^2=CH_3$, $R^3$=isopropyl, $R^4$=H, $R^5$=p-fluorophenyl]

EXAMPLE 15.1

1-Isopropyl-2-methyl-3-methoxycarbonyl-4-(4-fluorophenyl)-1H-pyrrole

[Formula XVIII with $R^2=CH_3$, $R^3$=isopropyl, $R^4$=H, $R^5$=p-fluorophenyl]

15 g (30 mmol) of the hydroxylamine from Example 9.1 are suspended in 500 ml of methanol, 3.6 g (60 mmol) of isopropylamine are added, and the mixture is stirred at 40° C. for 2 h and at 50° C. for 5 h. This results in the suspension being converted into a clear solution. The solvent is removed by distillation in vacuo, and the residue is chromatographed on silica gel using n-hexane/diethyl ether 4:1. 7.3 g of pale reddish-colored crystals, melting point 97°–99° C.

$^1$H NMR ($CDCl_3$): δ=1.42 (d, 6H, $C(CH_3)_2$, 2.53 (s, 3H, $CH_3$), 3.65 (s, 3H, $OCH_3$), 4.37 (sept., 1H, CH), 6.60 (s, 1H, arom. H), 6.80–7.46 (m, 4H, arom. H).

MS: $C_{16}H_{18}FNO_2$ (275.3) m/e=275 (M +), 244, 202, 201.

EXAMPLE 15.2

Process step D2 (Scheme 3)

1-Isopropyl-2-methyl-3-hydroxymethyl-4-(4-fluorophenyl)-1H-pyrrole

[Formula IV with $R^2=CH_3$, $R^3$=isopropyl, $R^4$=H, $R^5$=p-fluorophenyl]

1.6 g of colorless oil are obtained from 2.75 g of the methyl ester from Example 15.1 in analogy to Example 9.3.

MS: $C_{15}H_{18}FNO$ (247.3) m/e=247 (M+—OH , 188.

EXAMPLE 15.3

Process step D3 (Scheme 3)

1-Isopropyl-2-methyl-4-(4-fluorophenyl)-1H-pyrrole-3-carboxaldehyde

[Formula III with $R^2=CH_3$, $R^3$=isopropyl, $R^4$=H, $R^5$=p-fluorophenyl]

In analogy to Example 1.5, 1.3 g of colorless oil are obtained from 1.5 g of the alcohol from Example 15.2.

$^1$H NMR ($CDCl_3$): δ=1.43 (d, 6H, $C(CH_3)_2$), 2.60 (s, 3H, $CH_3$). 4.30 (sept 1H CH) 6.68 (s 1H arom. H) 6.9–7.56 (m, 4H, arom. H), 9.92 (s, 1H, CHO).

MS: $C_{15}H_{16}FNO$ (245) m/e=245 (M+), 202.

EXAMPLE 15.4

Process step Z1

3-[1-Isopropyl-2-methyl-4-(4-fluorophenyl)-1H-pyrrol-3-yl]-(E)-propenal

[Formula XI with $R^2=CH_3$, $R^3=$isopropyl, $R^4=H$, $R^5=$p-fluorophenyl]

In analogy to Example 1.(, 1.35 g of colorless crystals are obtained from 1.3 g cf the aldehyde from Example 15.3.

$^1$H NMR (CDCl$_3$): $\delta=1.47$ (d, 6H, C(CH$_3$)$_2$), 2.43 (s, 3H, CH$_3$), 4.42 (sept., 1H, CH), 6.20 (dd, J=16 and 7.8 Hz, 1H, =CH), 6.72 (s, 1H, arom. H), 6.9–7.5 (m, 4H, arom. H), 7.50 (d, J=16 Hz, 1H, =CH), 9.48 (d, 1H, CHO).

MS: C$_{17}$H$_{18}$FNO (271) m/e=271 (M+), 256, 242, 200.

EXAMPLE 15.5

Process step B1

Methyl 5(RS)-hydroxy-3-oxo-7-[1-isopropyl-2-methyl-4-(4-fluorophenyl)-1H-pyrrol-3-yl]hept-6(E)-enoate

[Formula XII with $R^1=CH_3$, $R^2=CH_3$, $R^3=$isopropyl, $R^4=H$, $R^5=$p-fluorophenyl]

In analogy to Example 1.7, 1.42 g of pale yellow oil are obtained from 1.2 g of the aldehyde from Example 15.4.

$^1$H NMR (CDCl$_3$, 270 MHz): $\delta=1.44$ (d+signal overlapping, 8H, C(CH$_3$)$_2$+CH$_2$), 1.58 (s, broad, 1H, OH), 2.37 (s, 3H, CH$_3$, 3.58 (s, 2H, CH$_2$), 3.75 (s, 3H, OCH$_3$), 4.35 (sept., 1H, CH), 6.02 (d, J=16.0 Hz, 1H, =CH), 6.27 (dd, J=16.0 and 11.2 Hz, 1H, =CH), 6.67 (s, 1H, arom. H), 7.06 (AA'BB', 2H, arom. H), 7.28 (AA'BB', 2H, arom. H).

MS: C$_{22}$H$_{26}$FNO$_4$ (387.4) m/e=387 (M+), 369, 272.

EXAMPLE 15.6

Process step B2

Methyl 3(RS),5(SR)-dihydroxy-7-[1-isopropyl-2-methyl-4-(4-fluorophenyl)-1H-pyrrol-3-yl]hept-6(E)-enoate

[Formula I with AB=trans-HC=CH, $R^2=CH_3$, $R^2=CH_3$, $R^3=$isopropyl, $R^4=H$, $F^5=$p-fluorophenyl]

In analogy to Example 1.8, 803 mg of pale yellow oil are obtained from 1.42 g of the 8-keto ester from Example 15.5.

$^1$H NMR (C$_6$D$_6$, 270 MHz): $\delta=0.98$ (d, 6H, C(CH$_3$)$_2$, 1.40 (dt, 1H, CH$_2$), 1.68 (dt, 1H, CH$_2$), 2.05 (s, 3H, CH$_3$), 2.09 (dd, partial overlap, 1H, CH$_2$), 2.27 (dd, 1H, CH$_2$), 3.27 (s, 3H, OCH$_3$), 3.73 (sept., 1H, CH), 4.14 (m, 1H, CH), 4.34 (m, 1H, CH), 5.72 (dd, J=16.0 and 7.0 Hz, 1H, =CH) 6.50 (s, 1H, arom. H), 6.73 (d, J=16.0 Hz, 1H, =CH), 6.98 (AA'BB', 2H, arom. H), 7.43 (AA'BB', 2H, arom. H).

MS C$_{22}$H$_{28}$FNO$_4$ (389.5) m/e=389 (M+), 272, 230.

EXAMPLE 16

Process step A8 (Scheme 1)

Sodium 3(RS),5(SR)-dihydroxy-7-[1-isopropyl-2-methyl-4-(4-fluorophenyl)-1H-pyrrol-3-yl]hept-6(E)-enoate

[Formula I with AB=trans —CH=CH, $R^1=$Na, $R^2=CH_3$, $R^3=$isopropyl, $R^4=H$, $R^5=$p-fluorophenyl]is obtained from the product of Example 15.6 in analogy to Example 4.

EXAMPLE 17

Process step A9 (Scheme 1)

Methyl 3(RS),5(RS)-dihydroxy-7-[1-isopropyl-2-methyl-4-(4-fluorophenyl)-1H-pyrrol-3-yl]heptanoate

[Formula I with AB=CH$_2$—CH$_2$, $R^1=CH_3$, $R^2=CH_3$, $R^3=$isopropyl, $R^4=H$, $R^5=$p-fluorophenyl]

is obtained from the product of Example 15.6 in analogy to Example 3.

$^1$H NMR (C$_6$D$_6$, 270 MHz): $\delta=1.02$ (2×d, 6H, C(CH$_3$)$_2$), 1.38 (dt, 2H, CH$_2$), 1.50–1.75 (m, 2H, CH$_2$), 1.97 (dd, 1H, CH$_2$), 2.10 (s, 3H, CH$_3$), 2.15 (dd, 1H, CH$_2$), 2.82 (m, 2H, CH$_2$), 3.27 (s, 3H, OCH$_3$), 3.70 (m, 1H, CH), 3.78 (sept., 1H, CH), 3.93 (m, 1H, CH), 6.58 (s, 1H, arom. H), 6.98 (AA'BB', 2H, arom. H), 7.39 (AA'BB', 2H, arom. H).

MS: C$_{22}$H$_{30}$FNO$_4$ (391) DCI m/e=392.2 (M+H+), 391 (M+), 360.2, 331.1, 230.

EXAMPLE 18

Process step A8 (Scheme 1)

Sodium 3(RS),5(RS)-dihydroxy-7-[1-isopropyl-2-methyl-4-(4-fluorophenyl)-1H-pyrrol-3-yl]heptanoate

[Formula I with AB=CH$_2$—CH$_2$. $R^1=CH_3$. $R^2=CH_3$, $R^3=$isopropyl, $R^4=H$, $R^5=$p-fluorophenyl]is obtained from the methyl ester of Example 17 in analogy to Example 4.

EXAMPLE 19

Synthesis of methyl 3(RS),5(SR)-dihydroxy-7-[1-cyclohexyl-2-isopropyl-4-(4-fluorophenyl)-1H-pyrrol-3-yl]hept-6(E)-enoate

[Formula I with AB=trans-HC=CH, $R^1=CH_3$, $R^2=$isopropyl, $R^3=$cyclohexyl, $R^4=H$, $R^5=$p-fluorophenyl]

EXAMPLE 19.1

3-Oxo-4-methylpentananilide

A solution of 47.4 g (0.3 mol) of ethyl 3-oxo-4-methylpentanoate, 27.93 g (0.3 mol) of aniline and 0.6 ml of glacial acetic acid in 360 ml of toluene is boiled under reflux with a water trap for 4 hours. The reaction mixture is cooled and then washed twice with 0.5 N hydrochloric acid, then twice with saturated sodium bicarbonate solution and then with saturated brine, and is dried and concentrated in vacuo. The residue is chromatographed on 1 kg of silica gel using toluene/ethyl acetate 10:1. 40.5 g (66% yield) of pale pink-colored oil.

$^1$H NMR (CDCl$_3$): $\delta=1.2$ (d, 6H), 2.8 (s, 2H), 3.65 (s, 2H), 7.0–7.75 (m, 5H, 9.1–9.4 (s, br., 1H).

MS: C$_{12}$H$_{15}$NO$_2$ (205) m/e=205 (M+), 93.

EXAMPLE 19.2

3-Cyclohexylamino-4-methylpent-2(E)-enanilide (Scheme 4 d)

A solution of 31.6 g (154 mmol) of the anilide from Example 19.1, 30.55 g (308 mmol) of cyclohexylamine and 1.5 ml of glacial acetic acid in 750 ml of toluene is boiled under reflux with a water trap for 20 hours. The solvent is removed in vacuo, and the residue is stirred with 150 ml of diisopropyl ether, whereupon crystallization starts. The solid s filtered off with suction and washed with petroleum ether. 27.1 g of colorless solid. a further 8.9 g from the mother liquor (yield 82%). The melting point was not sharp (123°–132° C.), but the NMR showed adequate purity.

$^1$H NMR (CDCl$_3$): $\delta=1.15$ (d, 6H), 1.0–2.1 (m, 10H), 2.7 (sept., 1H), 3.45 (m, 1H), 4.4 (s, 1H), 6.55 (m, 1H), 6.9–7.6 (m, 5H), 9.5 (s, br., 1H).

MS: C$_{18}$H$_{26}$N$_2$O (286) m/e=286 (M+) 194, 93.

EXAMPLE 19.3

1-Cyclohexyl-2-isopropyl-4-(4-fluorophenyl)-1H-pyrrole-3-carboxanilide

[Formula XIX with $R^2$=isopropyl, $R^3$=cyclohexyl, $R^{3'}$=phenyl, $R^4$=H, $R^5$=p-fluorophenyl]

In analogy to Example 11.1 a 52% yield of a colorless solid, melting point 215°–216° C. (not recrystallized), is obtained.

$^1$H NMR (CDCl$_3$): δ=0.9–2.2 (d+m, 16H), 3.5–4.3 (m, 2H), 6.65 (s, 1H), 6.8–7.6 (m, 10H).

MS: C$_{26}$H$_{29}$FN$_2$O (404) CI m/e=405 (M+H+), 312, 230.

EXAMPLE 19.4

Process step D$_4$ (Scheme 3)

N-methylanilide of 1-cyclohexyl-2-isopropyl-4-(4-fluorophenyl)-1H-pyrrole-3-carboxylic acid

[Formula XX with $R^2$=isopropyl, $R^3$=cyclohexyl, $R^{3'}$=phenyl, $R^4$=H, $R^5$=p-fluorophenyl]

In analogy to Example 5.3 a 98% yield of a colorless resinous solid, which crystallizes on prolonged standing, is obtained. Melting point 102°–105° C. (not recrystallized).

$^1$H NMR (CDCl$_3$): δ=1.35 (d, 3H), 1.50 (d, 3H), 1.1–2.2 (m, 11H), 3.25 (s, br., 3H), 3.95 (m, 1H), 6.4–7.4 (m, 10H).

MS: C$_{27}$H$_{31}$FN$_2$O (418) CI m/e=419 (M+H+), 312.

EXAMPLE 19.5

Process step D$_5$ (Scheme 3)

1-Cyclohexyl-2-isopropyl-3-hydroxymethyl-4-(4-fluorophenyl)-1H-pyrrole

[Formula IV with $R^2$=isopropyl, $R^3$=cyclohexyl, $R^4$=H, $R^5$=p-fluorophenyl]

In analogy to Example 5.4 a 67% yield of a colorless solid, melting point 114°–116° C. (not recrystallized), is obtained.

1H NMR (CDCl$_3$): =1.37 (d, 6H), 1.2–2.1 (m, 10H), 3.30 (sept., 1H), 3.96 (m, 1H), 4.38 (s, 2H), 6.70 (s, 1H), 6.95 (m, 2H), 7.47 (m, 2H).

MS: C$_{20}$H$_{26}$FNO (315) m/e=315 (M+), 300, 282, 200.

EXAMPLE 19.6

Process step D$_3$ (Scheme 3)

1-Cyclohexyl-2-isopropyl-4-(4-fluorophenyl)-1H-pyrrole-3-carbaldehyde

[Formula III with $R^2$=isopropyl, $R^3$=cyclohexyl, $R^4$=H, $R^5$=p-fluorophenyl]

1.06 g (1.1 mmol) of tris(triphenylphosphine)ruthenium(II) chloride are added at room temperature to a solution of 12.9 g (110 mmol) of N-methylmorpholine N-oxide (97% pure) in 110 ml of acetone (dried over potassium carbonate). The mixture is stirred for 20 min, and then a solution of 8.67 g (27.5 mmol) of the pyrrole alcohol from Example 19.5 in 200 ml of acetone is added dropwise. The reaction mixture is stirred with exclusion of air for 19 h, then filtered through a short, thick column of silica gel (about 500 ml of silica gel), and the column is thoroughly washed with ether. The combined filtrates are concentrated. 8.4 g (97% yield) of colorless crystals, melting point 134°–135° C. (not recrystallized), are obtained.

$^1$H NMR (CDCl$_3$):δ=1.45 (d, 6H), 1.1–2.2 (m, 10H), 3.55–4.35 (m+sept., 2H), 6.65 (s, 1H), 6.9–7.6 (m, 4H), 9.95 (s, 1H).

MS C$_{20}$H$_{24}$FNO (313) m/e=313 (M+), 298, 231, 216.

EXAMPLE 19.7

Process step Z2

β-[1-Cyclohexyl-2-isopropyl-4-(4-fluorophenyl)-1H-pyrrol-3-yl]-(E)-acrylonitrile

[Formula XVII with $R^2$=isopropyl, $R^3$=cyclohexyl, $R^4$=H, $R^5$=p-fluorophenyl]

In analogy to Example 9.5 a 96% yield of a pale yellow solid, melting point 130°–132° C. (not recrystallized), is obtained.

$^1$H NMR (CDCl$_3$): δ=1.40 (d, 6H), 1.2–2.1 (, 10H), 3.30 (sept., 1H), 4.00 (m, 1H), 4.95 (d, 1H), 6.60 (s, 1H), 6.9–7.4 (m, 4H), 7.55 (d, 1H).

MS: C$_{22}$H$_{25}$FN$_2$ (336) m/e=336 (M+), 321, 239.

EXAMPLE 19.8

Process step Z3

3-[1-Cyclohexyl-2-isopropyl-4-(4-fluorophenyl)-1H-pyrrol-3-yl]-(E)-propenal

[Formula XI with $R^2$=isopropyl, $R^3$=cyclohexyl, $R^4$=H, $R^5$=p-fluorophenyl]

In analogy to Example 9.5 an 81% yield of pale yellow crystals, melting point 124° C. (not recrystallized), is obtained.

$^1$H NMR (CDCl$_3$): δ=1.46 (d, 6H), 1.3–2.2 (m, 10H), 3.50 sept., 1H), 4.00 (m, 1H), 6.05 (dd, 1H), 6.65 (s, 1H), 6.9–7.5 (m, 4H), 7.65 (d, 1H), 9.50 (d, 1H).

MS: C$_{22}$H$_{26}$FNO (339) m/e=339 (M+), 296, 214.

EXAMPLE 19.9

Process step B1

Methyl 5(RS)-hydroxy-3-oxo-7-[1-cyclohexyl-2-isopropyl-4-(4-fluorophenyl)-1H-pyrrol-3-yl]hept-6(E)-enoate

[Formula XII with $R^1$=CH$_3$, $R^2$=isopropyl, $R^3$=cyclohexyl, $R^4$=H, $R^5$=p-fluorophenyl]is obtained in 82% yield in analogy to Example 1.7.

$^1$H NMR (CD$_2$Cl$_2$): δ=1.35 (d, 6H), 1.3–2.3 (m, 10H), 2.35 (d, 1H), 2.65 (d, 2H), 3.30 (sept., 1H), 3.50 (s, 2H), 3.70 (s, 3H), 4.00 (m, 1H), 4.60 (m, 1H), 5.35 (dd, 1H), 6.65 (s, 1H), 6.65 (d, 1H , 6.85–7.50 (m, 4H).

MS: C$_{27}$H$_{34}$FNO$_4$ (455) m/e=455 (M+) 437, 340, 296, 214.

EXAMPLE 19.10

Process step B2

Methyl 3(RS),5(SR)-dihydroxy-7-[1-cyclohexyl-2-isopropyl-4(4-fluorophenyl)-1H-pyrrol-3-yl]hept-6(E)-enoate

[Formula I with AB=trans-HC=CH, $R^1$=CH$_3$, $R^2$=isopropyl, $R^3$=cyclohexyl, $R^4$=H, $R^5$=p-fluorophenyl]is obtained in analogy to Example 1.8.

EXAMPLE 20

Process step A8 (Scheme 1)

Sodium 3(RS),5(SR)-dihydroxy-7-[1-cyclohexyl-2-isopropyl-4(4-fluorophenyl)-1H-pyrrol-3-yl]hept-6(E)-enoate

[Formula I with AB=trans-HC=CH, $R^1$=Na, $R^2$=isopropyl, $R^3$=cyclohexyl, $R^4$=H, $R^5$=p-fluorophenyl]is obtained in analogy to Example 10 from the product from Example 19.10.

EXAMPLE 21

Process step A9 (Scheme 1)

Methyl 3(RS),5(RS)-dihydroxy-7-[1-cyclohexyl-2-isopropyl-4-(4-fluorophenyl)-1H-pyrrol-3-yl]heptanoate

[Formula I with AB=$CH_2$—$CH_2$, $R^1$=$CH_3$, $R^2$=isopropyl, $R^3$=cyclohexyl, $R^4$=H, $R^5$=p-fluorophenyl] is obtained in analogy to Example 3 from the product from Example 19.10.

EXAMPLE 22

Process step A8 (Scheme 1)

Sodium 3(RS),5(RS)-dihydroxy-7-[1-cyclohexyl-2-isopropyl-4-(4-fluorophenyl)-1H-pyrrol-3-yl]heptanoate

[Formula I with AB=$CH_2$—$CH_2$, $R^1$=Na, $R^2$=isopropyl, $R^3$=cyclohexyl, $R^4$=H, $R^5$=p-fluorophenyl] is obtained in analogy to Example 2 from the product from Example 21.

EXAMPLE 23

Synthesis of methyl 3(RS),5(SR)-dihydroxy-7-[1,2-diisopropyl-4-(4-fluorophenyl)-1H-pyrrol-3-yl]hept-6(E)-enoate

[Formula I with AB=trans-HC=CH, $R^1$=$CH_3$, $R^2$=isopropyl, $R^3$=isopropyl, $R^4$=H, $R^5$=p-fluorophenyl]

EXAMPLE 23.1.

3-Isopropylamino-4-methylpent-2(E)-enanilide (Scheme 4d)

35.7 g (174 mmol) of the anilide from Example 19.1 and 0.6 ml of glacial acetic acid are dissolved in 600 ml of toluene. The mixture was boiled under reflux with a water trap while 20.6 g (348 mmol) of isopropylamine were very slowly added dropwise. After refluxing for 16 hours, the mixture was concentrated and cooled. The crystals were stirred with diisopropyl ether/petroleum ether 1:1. The solid was filtered off with suction and washed with petroleum ether. 27 g of colorless solid, melting point 151°–153° C. A further 1.9 g, melting point 148°–150° C., were obtained from the mother liquor.

$^1$H NMR (CDCl$_3$): δ=1.1 (d, 6H), 1.25 (d, 6H), 2.73 (sept., 1H), 3.8 (m, 1H), 4.43 (s, 1H), 6.7 (s, 1H), 6.9–7.6 (m, 5H), 9.1–9.6 (s, br., 1H).

MS: $C_{15}H_{22}N_2O$ (246) CI m/e=247 (M+H$^+$), 154.

EXAMPLE 23.2

1,2-Diisopropyl-4-(4-fluorophenyl)-1H-pyrrole-3-carboxanilide

[Formula XIX with $R^2$=isopropyl, $R^3$=isopropyl, $R^{3'}$=phenyl, $R^4$=H, $R^5$=p-fluorophenyl]

In analogy to Example 11.1 a 50% yield of a colorless solid, melting point 131°–133° C. (not recrystallized), is obtained.

$^1$H NMR (CDCl$_3$): δ=1.45 (d, 6H), 1.55 (d, 6H), 3.75 (sept., 1H), 4.60 (sept., 1H), 6.70 (s, 1H), 6.9–7.6 (m, 10H).

MS: $C_{23}H_{25}FN_2O$ (364) m/e=364 (M+), 272, 230.

EXAMPLE 23.3

Process step D4 (Scheme 3)

N-methylanilide of 1,2-diisopropyl-4-(4-fluorophenyl)-1H-pyrrole-3-carboxylic acid

[Formula XX with $R^2$=isopropyl, $R^3$=isopropyl, $R^{3'}$=phenyl, $R^4$=H, $R^5$=p-fluorophenyl]

In analogy to Example 5.3 a 73% yield of an oil is obtained.

$^1$H NMR (CDCl$_3$): δ=1.40 (d, 12H), 3.23 (s+sept., 4H), 4.40 (sept., 1H), 6.50 (s, 1H), 6.5–7.5 (m, 9H).

MS: $C_{24}H_{27}FN_2O$ (378) m/e=378 (M+), 272, 91.

EXAMPLE 23.4

Process step D$_5$ (Scheme 3)

1,2-Diisopropyl-3-hydroxymethyl-4-(4-fluorophenyl)-1H-pyrrole

[Formula IV with $R^2$=isopropyl, $R^3$=isopropyl, $R^4$=H, $R^5$=p-fluorophenyl]

In analogy to Example 5.4 a 75% yield of a pale yellow oil, which slowly crystallizes, is obtained.

$^1$H NMR (CDCl$_3$): δ=1.2–1.6 (m, 12H), 2.35 (s, br., 1H), 3.33 (sept., 1H), 4.40 (s, 2H), 4.50 (sept., 1H), 6.70 (s, 1H), 6.8–7.65 (m, 4H).

MS: $C_{17}H_{22}FNO$ (275) CI m/e=275 (M+), 258, 242, 200.

EXAMPLE 23.5

Process step D3 (Scheme 3)

1,2-Diisopropyl-4-(4-fluorophenyl)-1H-pyrrole-3-carbaldehyde

[Formula III with $R^2$=isopropyl, $R^3$=isopropyl, $R^4$=H, $R^5$=p-fluorophenyl]

In analogy to Example 19.6 an 87% yield of a yellowish oil is obtained.

$^1$H NMR (CDCl$_3$): δ=1.43 (d, 6H), 1.47 (d, 6H), 3.80 (sept., 1H), 4.57 (sept., 1H), 6.62 (s, 1H), 7.06 (m, 2H), 7.37 (m, 2H), 9.89 (s, 1H).

MS: $C_{17}H_{20}FNO$ (273) m/e=273 (M+), 258, 244.

EXAMPLE 23.6

Process step Z2

β-[1,2-Diisopropyl-4-(4-fluorophenyl)-1H-pyrrol-3-yl]-(E)-acrylonitrile

[Formula XVII with $R^2$=isopropyl, $R^3$=isopropyl, $R^4$=H, $R^5$=p-fluorophenyl]

In analogy to Example 9.5 a 91% yield of crystals of melting point 121°–123° C. (not recrystallized) is obtained.

$^1$H NMR (CDCl$_3$): δ=1.43 (2×d, 12H), 3.30 (sept., 1H), 4.50 (sept., 1H), 4.93 (c, 1H), 6.60 (s, 1H), 6.9–7.4 (m, 4H), 7.53 (d, 1H).

MS: $C_{19}H_{21}N_2F$ (296) m/e=296 (M+), 281, 256, 239.

EXAMPLE 23.7

Process step Z3

3-[1,2-diisopropyl-4-(4-fluorophenyl)-1H-pyrrol-3-yl]-(E)-propenal

[Formula XI with $R^2$=isopropyl, $R^3$=isopropyl, $R^4$=H, $R^5$=p-fluorophenyl]

In analogy to Example 9.5 a 70% yield of a colorless solid, melting point 119°–121° C. (not recrystallized), is obtained.

$^1$H NMR (CDCl$_3$): δ=1.45 (2×d, 12H), 3.45 (sept., 1H), 4.53 (sept., 1H), 6.00 (dd, 1H), 6.65 (s, 1H), 6.9–7.5 (m, 4H), 7.63 (d, 1H), 9.45 (d, 1H).

MS: $C_{19}H_{22}FNO$ (299) m/e=299 (M+), 256, 214.

EXAMPLE 23.8

Process step B1

Methyl 5(RS)-hydroxy-3-oxo-7-[1,2-diisopropyl-4-(4-fluorophenyl)-1H-pyrrol-3-yl]hept-6(E)-enoate

[Formula XII with $R^1=CH_3$, $R^2=$isopropyl, $R^3=$isopropyl, $R^4=H$, $R^5=$p-fluorophenyl]is obtained in 80% yield in analogy to Example 1.7 from the product of Example 23.7.

$^1$H NMR (CD$_2$Cl$_2$): δ=1.36 (d, 6H), 1.42 (d, 6H), 2.37 (d, 1H), 2.68 (m, 2H), 3.30 (sept., 1H), 3.48 (s, 2H), 3.70 (s, 3H), 4.44 (sept., 1H), 4.59 (m, 1H), 5.32 (dd, 1H), 6.62 (d, 1H), 6.62 (s, 1H), 7.00 (m, 2H), 7.30 (m, 2H).

MS: $C_{24}H_{30}FNO_4$ (415) m/e=415 (M$^+$), 397, 300, 256.

EXAMPLE 23.9

Process step B2

Methyl 3(RS),5(SR)-dihydroxy-7-[1,2-diisopropyl-4-(4-fluorophenyl)-1H-pyrrol-3-yl]hept-6(E)-enoate

[Formula I with AB=trans-HC=CH, $R^1=CH_3$, $R^2=$isopropyl, $R^3=$isopropyl, $R^4=H$, $R^5=$p-fluorophenyl]is obtained in analogy to Example 1.8.

EXAMPLE 24

Process step A8 (Scheme 1)

Sodium 3(RS),5(SR)-dihydroxy-7-[1,2-diisopropyl-4-(4-fluorophenyl)-1H-pyrrol-3-yl]hept-6(E)-enoate

[Formula I with AB=trans-HC=CH, $R^1=Na$, $R^2=$isopropyl, $R^3=$isopropyl, $R^4=H$, $R^5=$p-fluorophenyl]is obtained in analogy to Example 10 from the product from Example 23.9.

EXAMPLE 25

Process step A9 (Scheme 1)

Methyl 3(RS),5(RS)-dihydroxy-7-[1,2-diisopropyl-4-(4-fluorophenyl)-1H-pyrrol-3-yl]heptanoate

[Formula I with AB=CH$_2$—CH$_2$, $R^1=CH_3$, $R^2=$isopropyl, is obtained in analogy to Example 3 from the product from Example 23.9.

EXAMPLE 26

Process step A8 (Scheme 1)

Sodium 3(RS),5(RS)-dihydroxy-7-[1,2-diisopropyl-4-(4-fluorophenyl)-1H-pyrrol-3-yl]heptanoate

[Formula I with AB=CH$_2$—CH$_2$, $R^1=Na$, $R^2=$isopropyl, $R^3=$isopropyl, $R^4=H$, $R^5=$p-fluorophenyl]is obtained in analogy to Example 2 from the product of Example 25.

We claim:

1. 7-[1H-pyrrol-3-yl]-substituted 3,5-dihydroxyheptanoic acid derivatives of the formula I

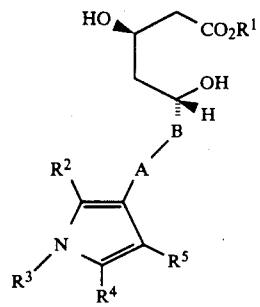

and corresponding δ-lactones of the formula II

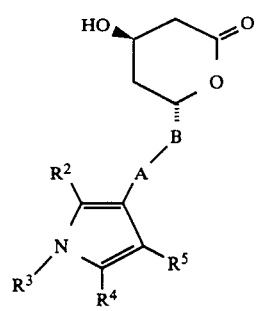

in which

A—B denotes —CH$_2$—CH$_2$—, $R^1$ denotes a pharmacologically tolerated alkali or alkaline earth metal cation, $R^2$ denotes isopropyl, $R^3$ denotes phenyl or isopropyl, $R^4$ denotes H, and $R^5$ denotes p-fluorophenyl.

2. A compound as claimed in claim 1, wherein in formula I, $R^1$ denotes Na.

3. An antihypercholesterdemic pharmaceutical composition comprising a compound of claim 1 and an inert pharmaceutically acceptable carrier.

4. A method for treating hypercholesterolemia comprising administering a compound of claim 1 in a pharmaceutically effective amount.

* * * * *